(12) United States Patent
Nekado et al.

(10) Patent No.: US 10,836,747 B2
(45) Date of Patent: Nov. 17, 2020

(54) ETHANE-SULFONATE SALT OF QUINOLINE DERIVATIVE

(71) Applicant: ONO PHARMACEUTICAL CO., LTD., Osaka (JP)

(72) Inventors: Takahiro Nekado, Osaka (JP); Hideomi Kijima, Osaka (JP); Shizuka Ono, Osaka (JP); Toshihiko Nishiyama, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/480,514

(22) PCT Filed: Jan. 25, 2018

(86) PCT No.: PCT/JP2018/002250
§ 371 (c)(1),
(2) Date: Jul. 24, 2019

(87) PCT Pub. No.: WO2018/139527
PCT Pub. Date: Aug. 2, 2018

(65) Prior Publication Data
US 2019/0389837 A1    Dec. 26, 2019

(30) Foreign Application Priority Data

Jan. 26, 2017    (JP) ................. 2017-011835

(51) Int. Cl.
*C07D 401/14*    (2006.01)
*A61K 31/4709*    (2006.01)

(52) U.S. Cl.
CPC ........ *C07D 401/14* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 9,562,060 B2 | 2/2017 | Cheng et al. | |
| 9,573,935 B2 | 2/2017 | Inukai et al. | |
| 9,994,549 B2 | 6/2018 | Inukai et al. | |
| 2002/0048610 A1 | 4/2002 | Cima et al. | |
| 2007/0060613 A1 | 3/2007 | Kim | |
| 2008/0312232 A1 | 12/2008 | Kim et al. | |
| 2009/0274693 A1 | 11/2009 | Gilmer et al. | |
| 2009/0306103 A1 | 12/2009 | Boyer et al. | |
| 2011/0053931 A1 | 3/2011 | Gaudino et al. | |
| 2011/0092503 A1 | 4/2011 | Ullrich et al. | |
| 2011/0118252 A1 | 5/2011 | Kim et al. | |
| 2012/0070413 A1 | 3/2012 | Kim et al. | |
| 2013/0142790 A1 | 6/2013 | Gilmer et al. | |
| 2013/0150363 A1 | 6/2013 | Gilmer et al. | |
| 2014/0018365 A1 | 1/2014 | Schultz-Fademrecht et al. | |
| 2014/0206679 A1 | 7/2014 | Cheng et al. | |
| 2014/0275077 A1 | 9/2014 | Dandu et al. | |
| 2016/0168121 A1 | 6/2016 | Inukai et al. | |
| 2017/0088542 A1 | 3/2017 | Inukai et al. | |

FOREIGN PATENT DOCUMENTS

| | | |
|---|---|---|
| CN | 101528702 A | 9/2009 |
| CN | 102083824 A | 6/2011 |
| CN | 103124729 A | 5/2013 |
| EP | 3 026 045 A1 | 6/2016 |
| JP | 2003-519698 A | 6/2003 |
| JP | 2008-539275 A | 11/2008 |
| JP | 2009-537632 A | 10/2009 |
| JP | 2009-539878 A | 11/2009 |
| JP | 2010-178651 A | 8/2010 |
| JP | 2011-517689 A | 6/2011 |
| JP | 2014-533287 A | 12/2014 |
| WO | 2006/116713 A1 | 11/2006 |
| WO | 2007/033196 A1 | 3/2007 |
| WO | 2007/146824 A2 | 12/2007 |
| WO | 2008/048375 A1 | 4/2008 |
| WO | 2009/137429 A1 | 11/2009 |
| WO | 2009/140549 A1 | 11/2009 |
| WO | 2010/039248 A1 | 4/2010 |
| WO | 2012/011548 A1 | 1/2012 |
| WO | 2012/028332 A1 | 3/2012 |
| WO | 2012/080729 A2 | 6/2012 |
| WO | 2013/074633 A1 | 5/2013 |
| WO | 2015/012298 A1 | 1/2015 |

OTHER PUBLICATIONS

Morissette et al., Advanced Drug Delivery Reviews, 56, pp. 275-300 (Year: 2004).*
Registry (STN) [online], Jan. 16, 2001, RN 314026-41-0, [retrieval date Aug. 6, 2014], Total 1 page.
Search Report dated Feb. 9, 2016, issued by the International Searching Authority in International Application No. PCT/JP2015/086050 (PCT/ISA/210).
Written Opinion dated Feb. 9, 2016, issued by the International Searching Authority in International Application No. PCT/JP2015/086050 (PCT/ISA/237).
International Searching Authority, Search Report dated Aug. 19, 2014, issued in International Application No. PCT/JP2014/069419 (PCT/ISA/210).
International Searching Authority, Written Opinion dated Aug. 19, 2014, issued in International Application No. PCT/JP2014/069419 (PCT/ISA/237).

(Continued)

*Primary Examiner* — Zinna Northington Davis
(74) *Attorney, Agent, or Firm* — Sughrue Mion, PLLC

(57) ABSTRACT

The present invention relates to an ethane-sulfonate salt of N-{5-[(6,7-dimethoxy-4-quinolinyl)oxy]-2-pyridinyl}-2,5-dioxo-1-phenyl-1,2,5,6,7,8-hexahydro-3-quinolinecarboxamide, which has an Axl-inhibiting activity and is useful as a prophylactic and/or therapeutic agent for immune diseases, cancer and the like, a crystal thereof, and a pharmaceutical composition thereof.

12 Claims, 12 Drawing Sheets

(56) References Cited

OTHER PUBLICATIONS

Zhihui Wang et al. "Mathematical modeling in cancer drug discovery" Drug Discovery Today, vol. 19, No. 2, Feb. 2014, (pp. 145-150).
Zhang, et al.; "Discovery of novel type II c-Met inhibitors based on BMS-777607", European Journal of Medicinal Chemistry, vol. 80, Apr. 2014, 13 pages total.
Xiaoliang Wu et al. "AXL kinase as a novel target for cancer therapy" Oncotarget, vol. 5, No. 20, Oct. 16, 2014, (pp. 9546-9563).
Udaya Kiran Marelli et al. "Tumor targeting via integrin ligands" Frontiers in Oncology, vol. 3, Article 222, Aug. 30, 2013, (pp. 1-12).
T. Fujimori et al. "The Axl receptor tyrosine kinase is a discriminator of macrophage function in the inflamed lung" Mucosal Immunology, vol. 8, No. 5, Sep. 2015, (pp. 1021-1030).
Anna Zagórska et al. Diversification of TAM receptor tyrosine kinase function Nature Immunology vol. 15, No. 10, Oct. 2014, (pp. 920-930).
Brooke M. VandenBrink et al. "Evaluation of CYP2C8 Inhibition In Vitro: Utility of Montelukast as a Selective CYP2C8 Probe Substrate" The American Society for Pharmacology and Experimental Therapeutics, vol. 31, No. 9, 2011, (p. 1546-1554).
Carla V Rothlin et al. "TAM receptor signaling and autoimmune disease", Current Opinion in Immunology, vol. 22 2010, (pp. 740-746).
Carla V. Rothlin et al. "TAM Receptor Signaling in Immune Homeostasis" American review of Immunology, vol. 33, Jan. 14, 2015, (pp. 355-391).
Anette Fiebeler et al. "Growth Arrest Specific Protein 6/Axl Signaling in Human Inflammatory Renal Diseases" American Journal of Kidney Disease, vol. 43, No. 2, Feb. 2004, (pp. 286-295).
Rachel M.A. Linger et al. "TAM Receptor Tyrosine Kinases: Biologic Functions, Signaling, and Potential Therapeutic Targeting in Human Cancer", Advances in Cancer Research, 2008, (pp. 35-83).
Communication dated Feb. 27, 2018, issued by the USPTO in U.S. Appl. No. 15/539,530.
Allen G et al: "Identification of small molecule inhibitors of proline-rich tyrosine kinase 2 (Pyk2) with osteogenic activity in osteoblast cells", Bioorganic & Medicinal Chemistry Letters, vol. 19, No. 17, Sep. 1, 2009, XP026458526, pp. 4924-4928, (5 pages total).
Samit K Bhattacharya et al: "Identification of novel series of pyrazole and indole-urea based DFG-out PYK2 inhibitors", Bioorganic & Medicinal Chemistry Letters, vol. 22, No. 24, Dec. 1, 2012, XP055093905, pp. 7523-7529, (7 pages total).
Extended European Search Report dated Nov. 15, 2017, issued by the European Patent Office in European Application No. 15873185.1.
Lovering, et al.; "Identification of Type-II Inhibitors Using Kinase Structures", Chemical Biology and Drug Design, vol. 80, No. 5, Jun. 2012, 8 pages total.
European Intellectual Property Office, Communication dated Dec. 6, 2016 issued in European Application No. 14828976.2.
Communication dated Nov. 2, 2016, issued by the State Intellectual Property Office of the People's Republic of China in Chinese Patent Application No. 201480041780.2.
Related U.S. Appl. No. 15/539,530, filed Jun. 23, 2017.
Communication dated Feb. 6, 2019 issued by the United States Patent and Trademark Office in U.S. Appl. No. 16/237,275.
Communication dated May 23, 2019 issued by the United States Patent and Trademark Office in U.S. Appl. No. 16/237,275.
Communication dated May 30, 2019 issued by the United States Patent and Trademark Office in U.S. Appl. No. 16/237,275.
Communication dated Jun. 21, 2018 issued by the United States Patent and Trademark Office in U.S. Appl. No. 15/975,999.
Communication dated Oct. 10, 2018 issued by the United States Patent and Trademark Office in U.S. Appl. No. 15/975,999.
Communication dated Apr. 2, 2018 issued by the United States Patent and Trademark Office in U.S. Appl. No. 15/373,091.
Communication dated Sep. 15, 2017 issued by the United States Patent and Trademark Office U.S. Appl. No. 15/373,091.
Communication dated Apr. 10, 2018 issued by the United States Patent and Trademark Office in U.S. Appl. No. 15/373,091.
Communication dated Jan. 17, 2018 issued by the United States Patent and Trademark Office in U.S. Appl. No. 15/373,091.
Communication dated Feb. 13, 2018 issued by the United States Patent and Trademark Office in U.S. Appl. No. 15/373,091.
Communication dated May 6, 2016 issued by the United States Patent and Trademark Office in U.S. Appl. No. 14/906,993.
Communication dated Sep. 12, 2016 issued by the United States Patent and Trademark Office in U.S. Appl. No. 14/906,993.
Communication dated Dec. 15, 2016 issued by the United States Patent and Trademark Office in U.S. Appl. No. 14/906,993.
Communication dated Jan. 23, 2017 issued by the United States Patent and Trademark Office in U.S. Appl. No. 14/906,993.
Berge et al., "Pharmaceutical Salts", Journal of Pharmaceutical Sciences, vol. 66, No. 1, Jan. 1977, pp. 1-19, 19 pages total.
Kawaguchi et al., "Drug and crystal polymorphism", Journal of Human Environmental Engineering, vol. 4, No. 2, 2002, pp. 310-317, 10 pages total.
"Specifications and Test Methods of New Pharmaceuticals", PFSB / ELD Notification, No. 568, 2001, 25 pages total.
Ooshima, "Crystallization of Polymorphs and Pseudo-polymorphs and Its Control", Pharm Stage, vol. 6, No. 10, 2007, pp. 48-53, 9 pages total.
Takata, "API form screening and selection in drug discovery stage", Pharm Stage, vol. 6, No. 10, 2007, pp. 20-25, 10 pages total.
Yamano, "Approach to Crystal Polymorph in Process Research of New Drug", Synthetic Organic Chemistry , vol. 65, No. 9, 2007, pp. 907-913, 11 pages total.
Byrn et al., "Pharmaceutical Solids: A Strategic Approach to Regulatory Considerations", Pharmaceutical Research, vol. 12, No. 7, 1995, pp. 945-954, 10 pages total.
Korshunov, "Axl-dependent signalling: a clinical update", Clinical Science, vol. 122, 2012, pp. 361-368, 8 pages total.
Gjerdrum, "Axl is an essential epithelial-to-mesenchymal transition-induced regulator of breast cancer metastasis and patient survival", Proceedings of the National Academy of Sciences, vol. 107, No. 3, pp. 1124-1129, Jan. 19, 2010, 6 pages total.
Park et al., "Inhibition of the receptor tyrosine kinase Axl impedes activation of the FLT3 internal tandem duplication in human acute myeloid leukemia: implications for Axl as a potential therapeutic target", Blood, vol. 121, No. 11, Mar. 14, 2013, pp. 2064-2073, 11 pages total.
International Search Report dated Mar. 20, 2018 issued by the International Searching Authority in counterpart International Application No. PCT/JP2018/002250 (PCT/ISA/210).
Communication dated Oct. 21, 2019, issued by the European Patent Office in counterpart European Application No. 18744970.7.

\* cited by examiner

ETHANE-SULFONATE SALT OF QUINOLINE DERIVATIVE

TECHNICAL FIELD

The present invention relates to N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate (also referred to as esylate), and a crystal thereof (hereinafter, also abbreviated as a compound of the present invention) having an Axl inhibiting activity and being useful as an agent for preventing and/or treating immune system diseases, cancers, and the like, and relates to a pharmaceutical composition thereof.

BACKGROUND ART

Axl (also known as: UFO, ARK, Tyro7) is a receptor tyrosine kinase belonging to a TAM family (Axl, Mer and Tyro3) cloned from tumor cells. Gas6 (growth-arrest-specific protein 6) cloned as a gene specifically expressed at the time of cell proliferation arrest is known as a ligand for Axl. Axl activated by binding of Gas6 transfers a signal via phosphorylation. Since the signal activates an Erk1/2 pathway or a PI3K/Akt pathway, the activation of Axl is known to be involved in pathologic conditions of cancers, immune system diseases, circulatory system diseases, and the like (see, Non-Patent Literature 1).

In particular, the relation between Axl and various types of cancers is well known. For example, it is known that the expression of Axl is involved in metastasis and prognosis of breast cancer (see, Non-Patent Literature 2), and that Axl is involved in the pathologic conditions of acute myeloid leukemia (AML) (see Non-Patent Literature 3). Therefore, it is considered that compounds which inhibit the activation of Axl are useful for treatment of various type of cancers, immune system diseases, and circulatory system diseases.

As prior art of the compound of the present invention, a compound represented by the general formula (A):

[Chem. 1]

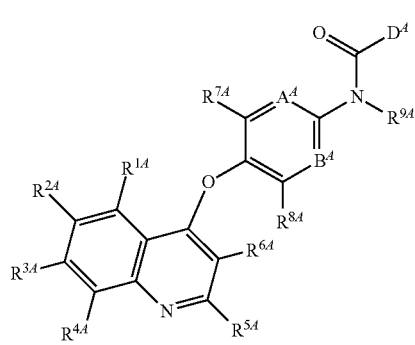

(A)

(wherein in the formula, $A^A$ represents $C-R^{10A}$ and N; $B^A$ represents $C-R^{11A}$ and N; $D^A$ represents the following heterocycle:

[Chem. 2]

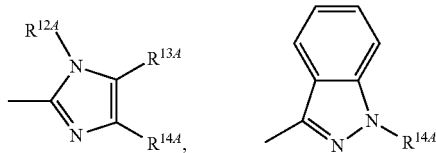

or the like; $R^{1A}$, $R^{4A}$, and $R^{88A}$ independently represent, —H, —F, —Cl, —Br, —I, —OH, —NH$_2$, —OCH$_3$, —OC$_2$H$_5$, and the like; $R^{2A}$ and $R^{3A}$ independently represent —R$^{88A}$ and the like; $R^{5A}$ and $R^{6A}$ may be the same as or different from each other, —H, —F, —Cl, —Br, —I, —CN, —NO$_2$, —CH$_3$, and the like; $R^{7A}$, $R^{8A}$, $R^{10A}$ and $R^{11A}$ may be the same as or different from each other, and represent —H, —F, —Cl, —Br, —I, —CN, —NO$_2$, —CH$_3$, and the like; $R^{9A}$ represents —H and the like; $R^{12A}$ represents —CN, phenyl, and the like; $R^{13A}$ represents —H, —F, —Cl, —Br, —I, —NO$_2$, —CH$_3$, and the like; $R^{14A}$ represents —H, —F, —Cl, —Br, —I, —NO$_2$, —CN, and the like (where the definitions of the groups are excerpted) is known to be an Axl inhibitor (see, Patent Literature 1).

Furthermore, a compound represented by the general formula (B):

[Chem. 3]

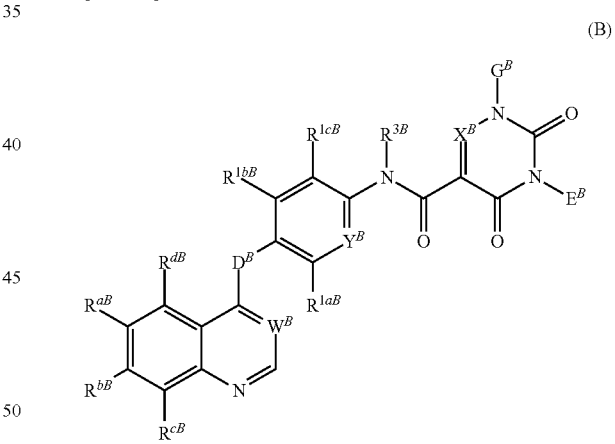

(B)

(wherein in the formula, $E^B$ and $G^B$ independently represent a hydrogen atom, a C1-6 alkyl group which may be substituted with 1 to 6 $R^{19B}$, a C6-11 aryl group which may be substituted with 1 to 6 $R^{19B}$, and the like; $X^B$ represents N or $C-R^{4B}$; $Y^B$ represents N or $C-R^{1dB}$; $D^B$ represents —O—, —S—, —NH—, and the like; $W^B$ represents CH or N; $R^{aB}$, $R^{bB}$, $R^{cB}$, $R^{dB}$, $R^{1aB}$, $R^{1bB}$, $R^{1cB}$, $R^{1dB}$ and $R^{4B}$ independently represent a hydrogen atom, —OR$^{110B}$, and the like; $R^{19B}$ represents a halogen atom, —CN, and the like; $R^{110B}$ represents a hydrogen atom, a C1-6 alkyl group which may be substituted with 1 to 6 $R^{129}$, and the like; $R^{129B}$ represents a C1-6 alkyl group, a C1-6 haloalkyl group, and the like (where the definitions of the groups are excerpted) is known to be an Axl inhibitor (see, Patent Literature 2).

On the other hand, a compound having a quinoline skeleton and represented by the formula (C):

[Chem. 4]

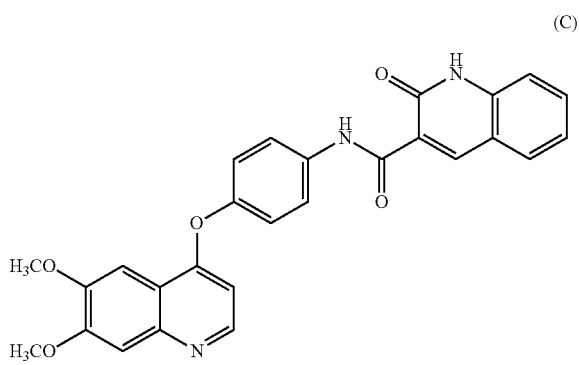

(C)

is known to have an ASK1 inhibiting activity and be an agent for preventing and/or treating amyotrophic lateral sclerosis (ALS) (see Patent Literature 3).

Furthermore, a compound represented by the general formula (D):

[Chem. 5]

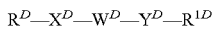

(D)

(wherein $R^D$ represents

[Chem. 6]

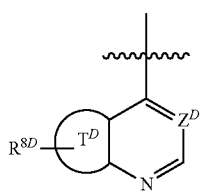

or the like; $T^D$ represents phenyl or the like; $Z^D$ represents N or $CR^{7D}$; $W^D$ represents a substituted or unsubstituted phenyl, substituted or unsubstituted 6-membered nitrogen-containing heteroaryl or the like; $X^D$ represents O, S, S(=O), or the like; $Y^D$ represents $-NR^{aD}C(=O)-(CR^{3D}R^{4D})_{pD}-$ or the like; $R^{aD}$ represents a hydrogen atom, an alkyl group, or the like; and $R^{1D}$ resents

[Chem. 7]

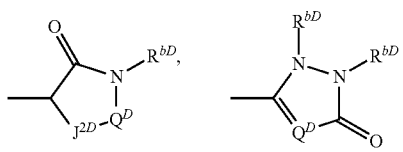

or the like; $J^{2D}$ represents O or $CR^{4aD}R^{4aD}$; $Q^D$ represents 1- to 5-membered saturated or partially unsaturated alkyl chain or the like; $R^{1D}$ represents optionally substituted phenyl or may be fused to optionally substituted 5- to 6-membered heterocycle; $R^{3D}$ and $R^{4D}$ each independently represents a hydrogen atom, an alkyl group, an aryl group, or the like; $R^{4aD}$ is absent or represents a hydrogen atom, a halogen atom, or the like; $R^{8D}$ represents one or more substituents independently selected from a hydrogen atom, a cyano group, a hydroxyl group, and the like (where the definitions of the groups are excerpted)) is known to be a c-Met inhibitor (see Patent Literature 4).

Furthermore, Patent Literature 5 describes N-{5-[(6,7-dimethoxy-4-quinolinyl)oxy]-2-pyridinyl}-2,5-dioxo-1-phenyl-1,2,5,6,7,8-hexahydro-3-quinolinecarboxamide that is a free base of the compound of the present invention (hereinafter, which may be abbreviated as a compound A) as Example 5. Furthermore, Patent Literature 5 mentions that the compound A is a compound having an Axl-selective inhibiting activity and a low CYP inhibitory action. On the other hand, Patent Literature 5 does not include specific examples of an acid addition salt of the compound A. Furthermore, with regard to ethanesulfonate of the compound A, there is neither description nor suggestion as to the fact that the ethanesulfonate has an Axl selective inhibiting activity and a low CYP inhibiting activity, and has a low hygroscopicity and is stable against humidity and light in the various acid addition salts of the compound A.

PRIOR ART LITERATURES

[Patent Literature 1] WO2012/028332(A)
[Patent Literature 2] WO2013/074633(A)
[Patent Literature 3] WO2012/011548(A)
[Patent Literature 4] WO2006/116713(A)
[Patent Literature 5] WO2015/012298(A)

Non-Patent Literatures

[Non-Patent Literature 1] Clinical Science, Vol. 122, p. 361-368, 2012
[Non-Patent Literature 2] Proceedings of the national academy of sciences of the United States of America, Vol. 107, No. 3, p. 1124-1129, 2010
[Non-Patent Literature 3] Blood, Vol. 121, p. 2064-2073, 2013

SUMMARY OF INVENTION

Technical Problem

A problem to be solved by the present invention is to provide a salt having an Axl-selective inhibiting activity, a low CYP inhibitory action, and a low hygroscopicity in various acid addition salts of a compound A, and being stable with respect to humidity and light, as an active pharmaceutical ingredient, in order to provide an agent for preventing and/or treating diseases related to expression of Axl, for example, cancer.

Solution to Problem

In order to solve the above-mentioned problem, the inventors of the present invention have keenly studied to find that the compound of the present invention is a salt having a low hygroscopicity in various acid addition salts of the compound A, and being stable with respect to humidity and light, and have completed the present invention.

The present invention provides, for example, the following embodiments.

[1] N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate,

[2] a crystal of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate,
[3] the crystal according to the above [2], wherein in a powder X-ray diffraction spectrum, the crystal has peaks at 2θ of about 7.3, about 7.9, about 9.1, about 10.7, about 11.2, about 12.5, about 13.4, about 15.6, about 16.2, about 16.5, about 17.7, about 18.0, about 18.4, about 19.1, about 20.1, about 20.8, about 21.2, about 21.5, about 22.4, about 23.0, about 23.6, and about 24.0,
[4] the crystal according to the [2] or [3], having characteristics of the powder X-ray diffraction spectrum chart shown in FIG. 1,
[5] the crystal according to the above [2] to [4], wherein in the differential scanning calorimetry, the crystal has an endothermic peak of an onset temperature of about 283° C. or a peak temperature of about 286° C.,
[6] the crystal according to the above [2] to [5], having characteristics of the differential scanning calorimetry chart shown in FIG. 2,
[7] a pharmaceutical composition including N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate or the crystal according to any one of the [2] to [6], and a pharmaceutically acceptable carrier,
[8] the pharmaceutical composition according to the above [7], which is an Axl inhibitor.
[9] the pharmaceutical composition according to the above [7], which is an agent for preventing and/or treating Axl-related disease,
[10] the pharmaceutical composition according the above [9], wherein the Axl-related disease is cancer, an immune system disease, or a circulatory system disease,
[11] the pharmaceutical composition according to the above [10], wherein the cancer is leukemia, malignant lymphoma, multiple myeloma, myelodysplastic syndromes, melanoma, uveal malignant melanoma, head and neck cancer, esophageal cancer, esophageal adenocarcinoma, stomach cancer, large intestine cancer, colon cancer, rectal cancer, liver cancer, gallbladder and bile duct cancer, biliary tract cancer, pancreatic cancer, thyroid cancer, lung cancer, breast cancer, ovarian cancer, cervical cancer, uterine body cancer, endometrial cancer, vaginal cancer, vulvar cancer, renal cell carcinoma, urothelial carcinoma, prostate cancer, testicular tumor, bone and soft tissue sarcoma, skin cancer, glioma, brain tumors, pleural mesothelioma or cancer of unknown primary,
[12] a method for preventing and/or treating Axl-related diseases, the method including administering an effective dose of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate, or the crystal according to any one of the above [2] to [6] to a mammalian animal,
[13] a crystal of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate or the crystal according to any one of the [2] to [6] for preventing and/or treating Axl-related disease,
[14] use of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate or the crystal according to any one of the above [2] to [6] for manufacturing an agent for preventing and/or treating Axl-related disease, and the like.

Advantageous Effects of Invention

The compound of the present invention has an Axl-selective inhibiting activity, a low CYP inhibitory action, a low hygroscopicity in various acid addition salts of compound A, and stable with respect to humidity and light, and, therefore, is useful as an active pharmaceutical ingredient of an agent for preventing and/or treating an Axl-related disease, for example, cancer, and having excellent stability.

DESCRIPTION OF EMBODIMENTS

The present invention will be described in detail hereinafter.

In the present invention, the phrase "having an Axl-selective inhibiting activity" means having an Axl-selective inhibiting activity with respect to tyrosine kinases other than Axl, in particular, with respect to KDR, DDR1, FLT4, and ROS. This property can avoid unpredictable side effect caused by inhibiting these tyrosine kinases other than Axl.

In the present invention, N-{5-[(6,7-dimethoxy-4-quinolinyl)oxy]-2-pyridinyl}-2,5-dioxo-1-phenyl-1,2,5,6,7,8-hexahydro-3-quinolinecarboxamide (compound A) means a compound represented by the following structural formula.

[Chem. 8]

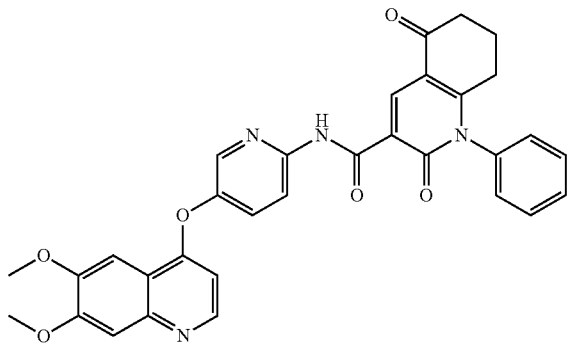

[Study of Acid Addition Salt of Compound A]

A compound A produced in the below-mentioned Example 5 and various acid counters are used to produce various acid addition salts of the compound A by the method described in the below-mentioned Examples. In a case where a crystal is obtained, the physical property data were measured by the following conditions.

[1] Powder X-Ray Diffraction Spectrum
<Measurement Conditions>
Device: BRUKER D8 DISCOVER with GADDS, manufactured by BRUKER axs,
Target: Cu,
Filter: Not used,
Voltage: 40 kV,
Electric current: 40 mA.
[2] Differential Scanning Calorimetry (DSC)
<Measurement Conditions>
Device: DSC 822e manufactured by METTLER TOLEDO,
Sample amount: 1 to 2 mg,
Sample cell: Aluminum pan 40 μL,
Flow amount of nitrogen gas: 40 mL/min,
Temperature rising rate: 10° C./min (25 to 240° C.).
[3] Evaluation of Hygroscopicity (DVS; Dynamic Vapor Sorption)
<Measurement Conditions>
Device: SGA-100 manufactured by TA Instruments,
Sample amount: 10 to 20 mg,
Measurement temperature: 25° C.,
Drying before measurement: 60° C., 1 hour,
Starting humidity: 0% RH,
Maximum humidity: 90% RH,
Step: 10% RH,
Equilibrium criteria: weight change rate in 5 minutes is 0.01% or less,
Sampling interval: 30 seconds,
Data recording interval: two minutes or time at which weight change rate become 0.01% or more.
[4] Conditions of PXRD-DSC Simultaneous Measurement
<Measurement Conditions>
Device: Rint Ultima manufactured by Rigaku,
Target: Cu,
Voltage: 40 kV,
Electric current: 50 mA,
Scanning speed: 10°/min,
Temperature rising rate: 2° C./min (from room temperature to 200° C.).

Figure 1:
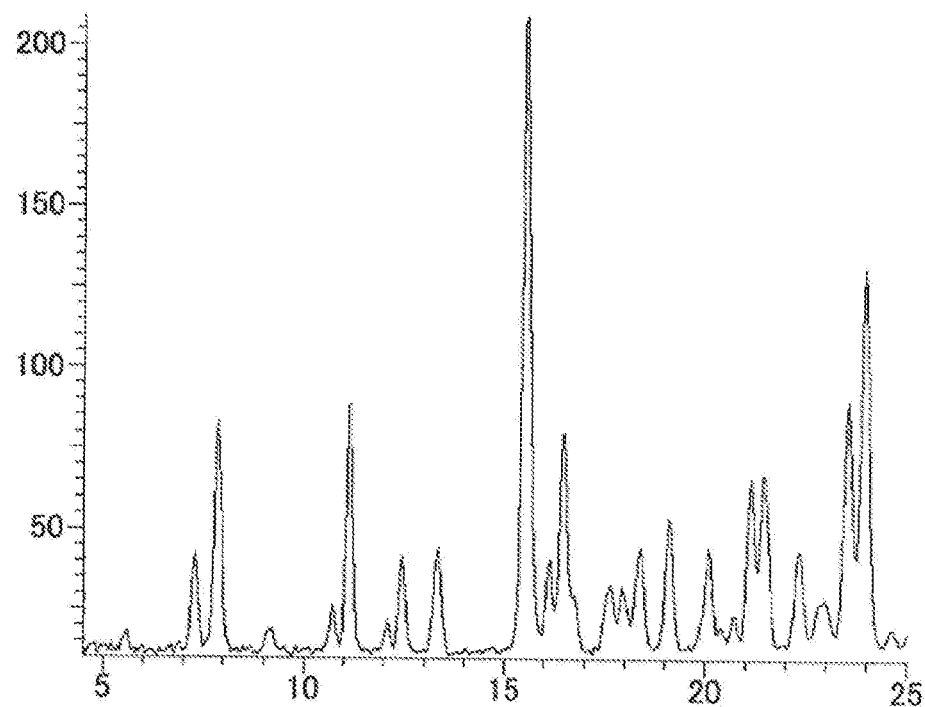
FIG. 1 is a powder X-ray diffraction spectrum chart showing a crystal of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate (in FIG. 1, the ordinate shows strength (counts) and the abscissa shows 2θ (°)).
Figure 2:
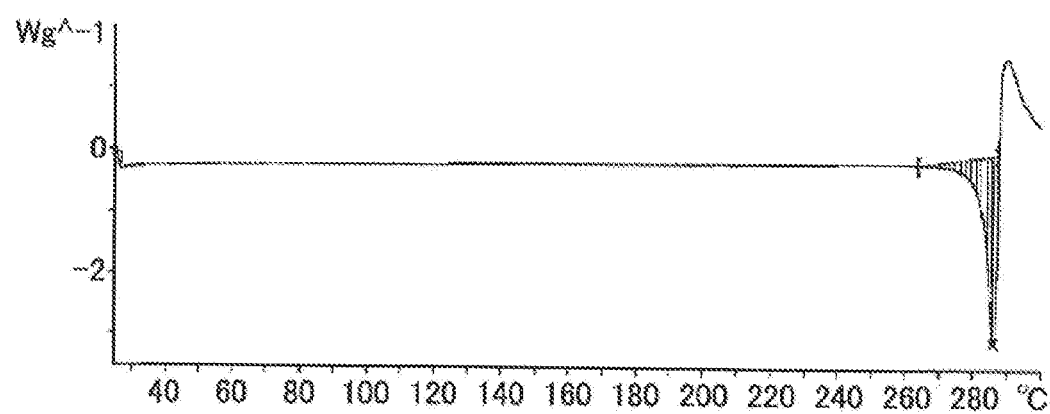
FIG. 2 is a differential scanning calorimetry (DSC) chart showing a crystal of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate.
Figure 3:
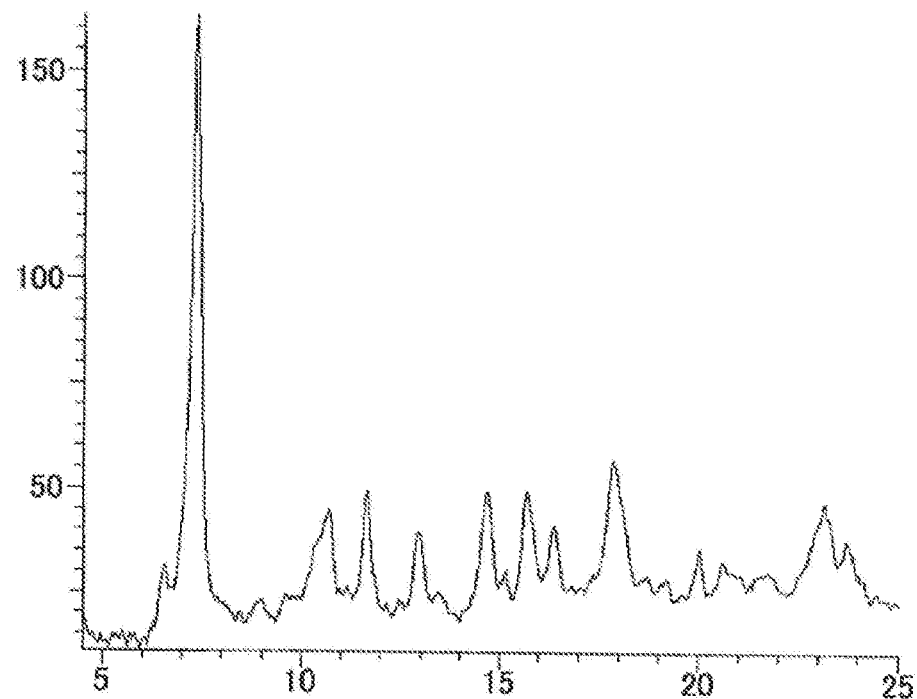
FIG. 3 is a powder X-ray diffraction spectrum chart showing a crystal (C-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide (in FIG. 3, the ordinate shows strength (counts) and the abscissa shows 2θ (°)).

The powder X-ray diffraction spectrum of the compound of the present invention is shown in FIG. 1, and the differential scanning calorimetry (DSC) chart of the compound of the present invention is shown in FIG. 2, respectively. Furthermore, the diffraction angle 2θ (°) and the relative strength (%) in the powder X-ray diffraction spectrum in the compound of the present invention are shown in the following Table 1.

TABLE 1

| Diffraction angle 2θ (°) | Relative strength (%) |
| --- | --- |
| 7.3 | 20.2 |
| 7.9 | 39.7 |
| 9.1 | 9.0 |
| 10.7 | 12.6 |
| 11.2 | 42.5 |
| 12.5 | 20.1 |
| 13.4 | 21.2 |
| 15.6 | 100.0 |
| 16.2 | 19.4 |
| 16.5 | 38.0 |

TABLE 1-continued

| Diffraction angle 2θ (°) | Relative strength (%) |
|---|---|
| 17.7 | 15.8 |
| 18.0 | 15.4 |
| 18.4 | 21.3 |
| 19.1 | 25.9 |
| 20.1 | 21.2 |
| 20.8 | 11.2 |
| 21.2 | 31.3 |
| 21.5 | 32.1 |
| 22.4 | 20.9 |
| 23.0 | 13.7 |
| 23.6 | 43.1 |
| 24.0 | 62.9 |

Furthermore, as shown in FIG. 2, the compound of the present invention showed endothermic peaks shown by the onset temperature of about 282.7° C. and the peak temperature of about 286.1° C., respectively.

The powder X-ray diffraction spectra of crystals of the compound A (C-crystal described in Example 5 (1), D-crystal described in Example 5 (2), E-crystal described in Example 5 (3), F-crystal described in Example 5 (4), G-crystal described in Example 5 (5), and H-crystal described in Example 5 (6)) are shown FIGS. 3, 5, 7, 9, 11, and 12, respectively. Furthermore, the differential scanning calorimetry (DSC) charts of crystals of the compound A (C-crystal described in Example 5 (1), D-crystal described in Example 5 (2), E-crystal described in Example 5 (3), F-crystal described in Example 5 (4), and H-crystal described in Example 5 (6)) are shown FIGS. 4, 6, 8, 10, and 13, respectively. Furthermore, among them, the diffraction angle 2θ (°) and relative strength (%) of the powder X-ray diffraction spectrum of the C-crystal of the compound A are shown in Table 2

TABLE 2

| Diffraction angle 2θ (°) | Relative strength (%) |
|---|---|
| 6.6 | 19.2 |
| 7.4 | 100.0 |
| 9.0 | 14.0 |
| 10.7 | 27.5 |
| 11.7 | 30.2 |
| 12.5 | 14.2 |
| 13.0 | 24.1 |
| 13.5 | 15.4 |
| 14.7 | 30.2 |
| 15.2 | 18.6 |
| 15.7 | 30.4 |
| 16.4 | 25.3 |
| 17.9 | 34.8 |
| 18.7 | 17.9 |
| 20.1 | 21.9 |
| 20.6 | 20.1 |
| 23.2 | 28.7 |
| 23.7 | 23.1 |

Figure 4:
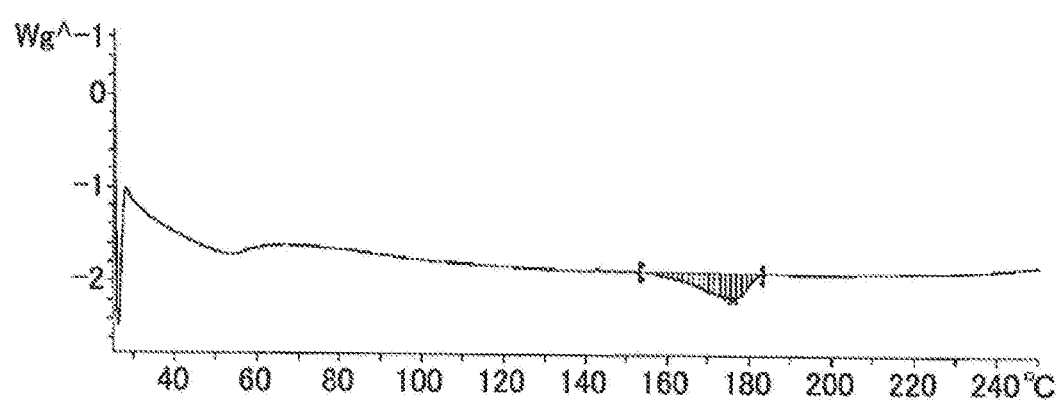
FIG. 4 is a differential scanning calorimetry (DSC) chart showing a crystal (C-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide.
Figure 5:
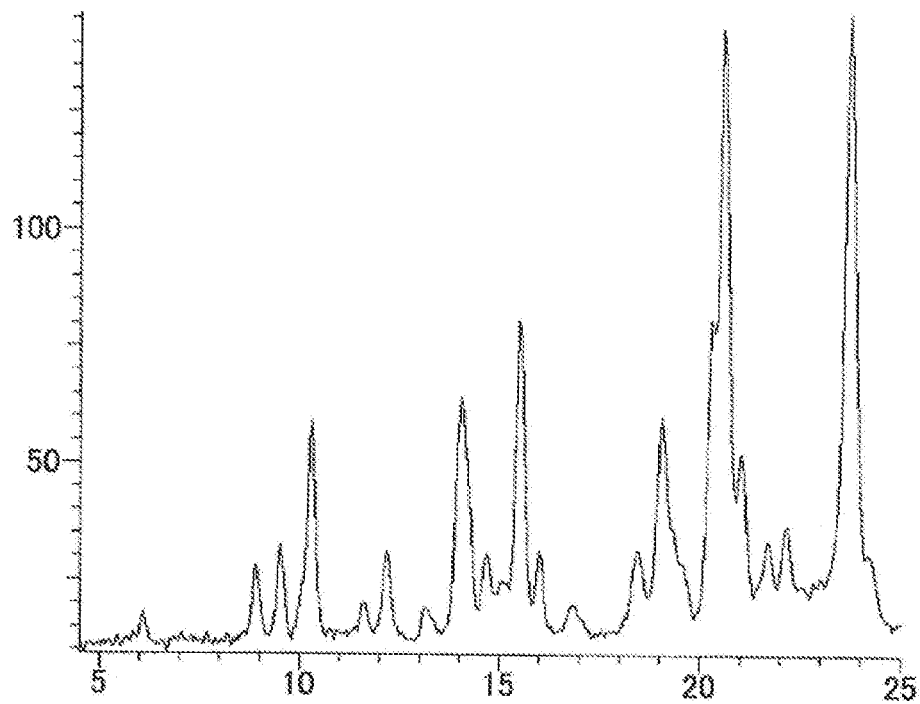
FIG. 5 is a powder X-ray diffraction spectrum chart showing a crystal (D-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide (in FIG. 5, the ordinate shows strength (counts) and the abscissa shows 2θ (°)).
Figure 6:
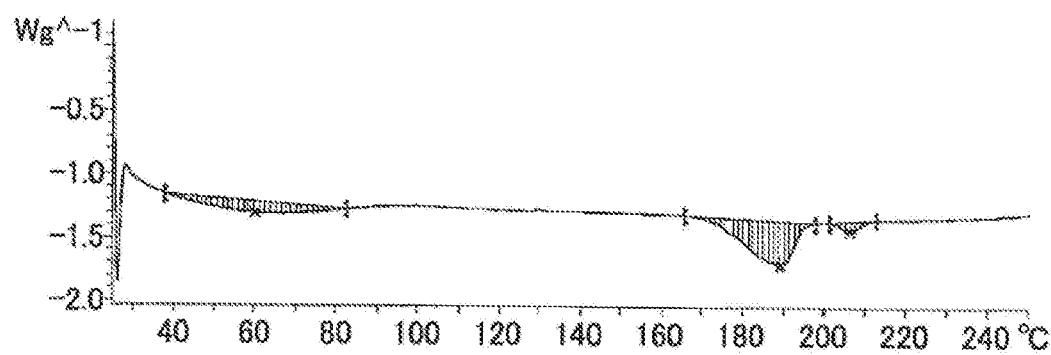
FIG. 6 is a differential scanning calorimetry (DSC) chart of a crystal (D-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide.
Figure 7:
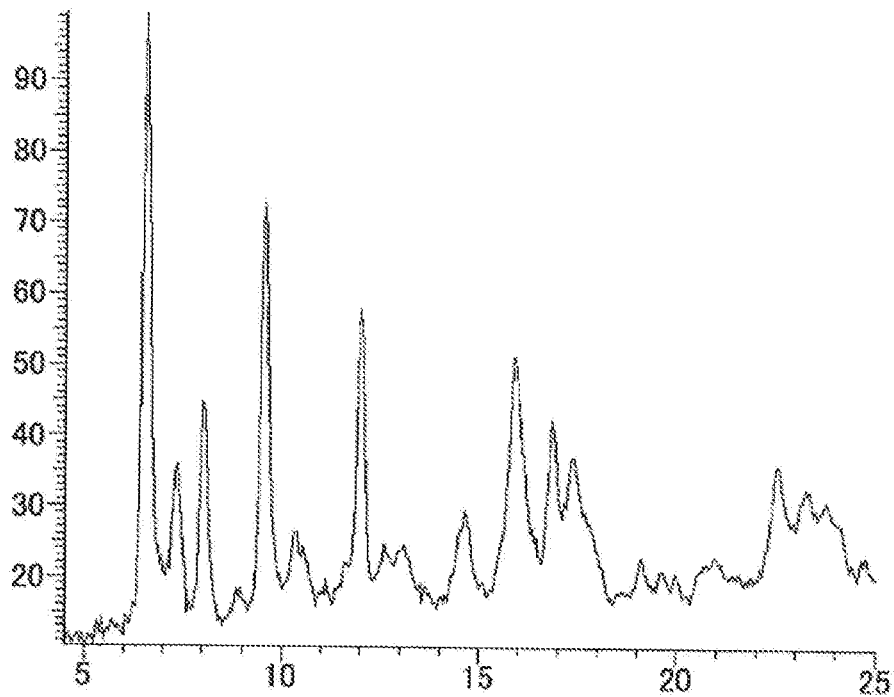
FIG. 7 is a powder X-ray diffraction spectrum chart showing a crystal (E-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide (in FIG. 7, the ordinate shows strength (counts) and the abscissa shows 2θ (°)).
Figure 8:
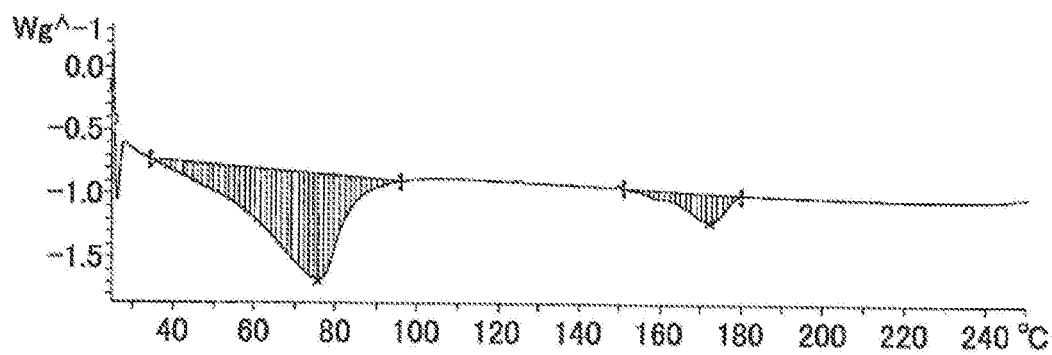
FIG. 8 is a differential scanning calorimetry (DSC) chart showing a crystal (E-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide.
Figure 9:
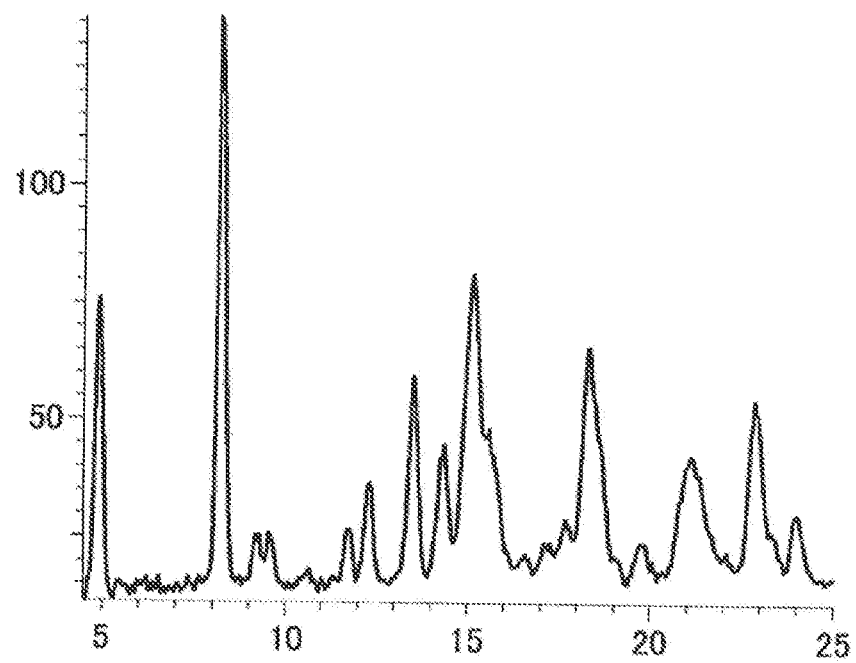
FIG. 9 is a powder X-ray diffraction spectrum chart showing a crystal (F-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide (in FIG. 9, the ordinate shows strength (counts) and the abscissa shows 2θ (°)).
Figure 10:
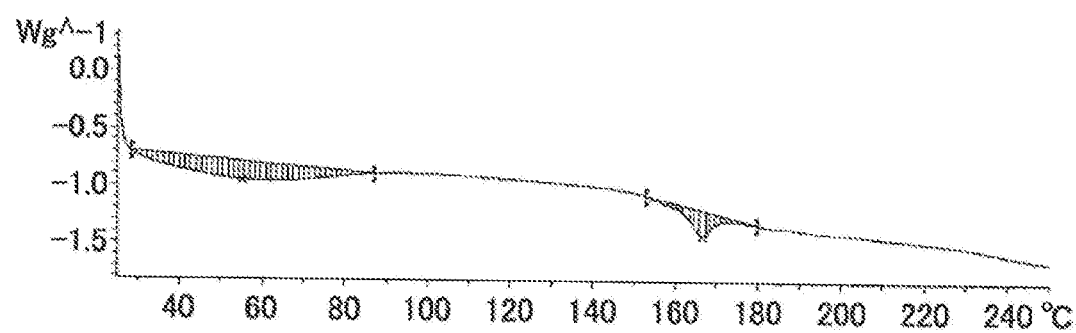
FIG. 10 is a differential scanning calorimetry (DSC) chart showing a crystal (F-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide.
Figure 11:
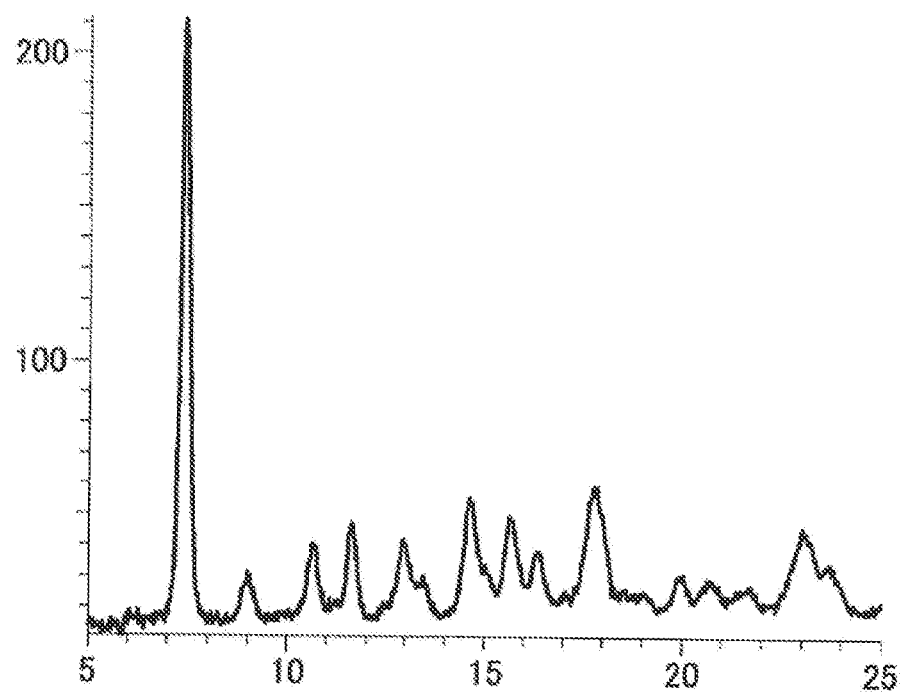
FIG. 11 is a powder X-ray diffraction spectrum chart showing a crystal (G-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide (in FIG. 11, the ordinate shows strength (counts) and the abscissa shows 2θ (°)).
Figure 12:
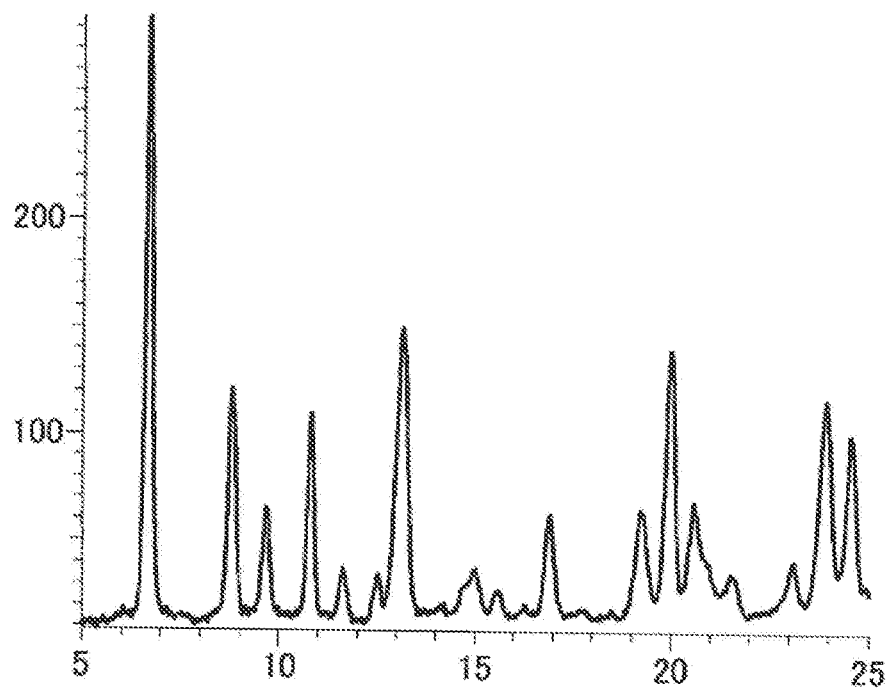
FIG. 12 is a powder X-ray diffraction spectrum chart showing a crystal (H-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide (in FIG. 12, the ordinate shows strength (counts) and the abscissa shows 2θ (°)).
Figure 13:
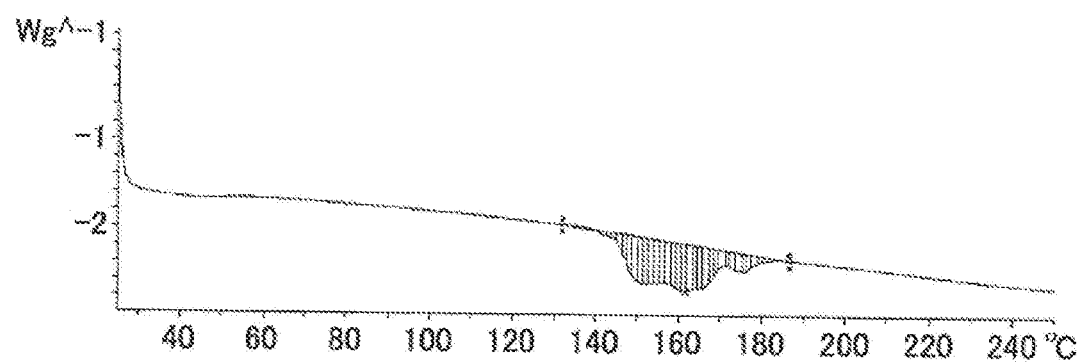
FIG. 13 is a differential scanning calorimetry (DSC) chart showing a crystal (H-type crystal) of N-{5-[(6,7-dimethoxy-4-quinolinyl)oxy]-2-pyridinyl}-2,5-dioxo-1-phenyl-1,2,5,6,7,8-hexahydro-3-quinolinecarboxamide.
Figure 14:
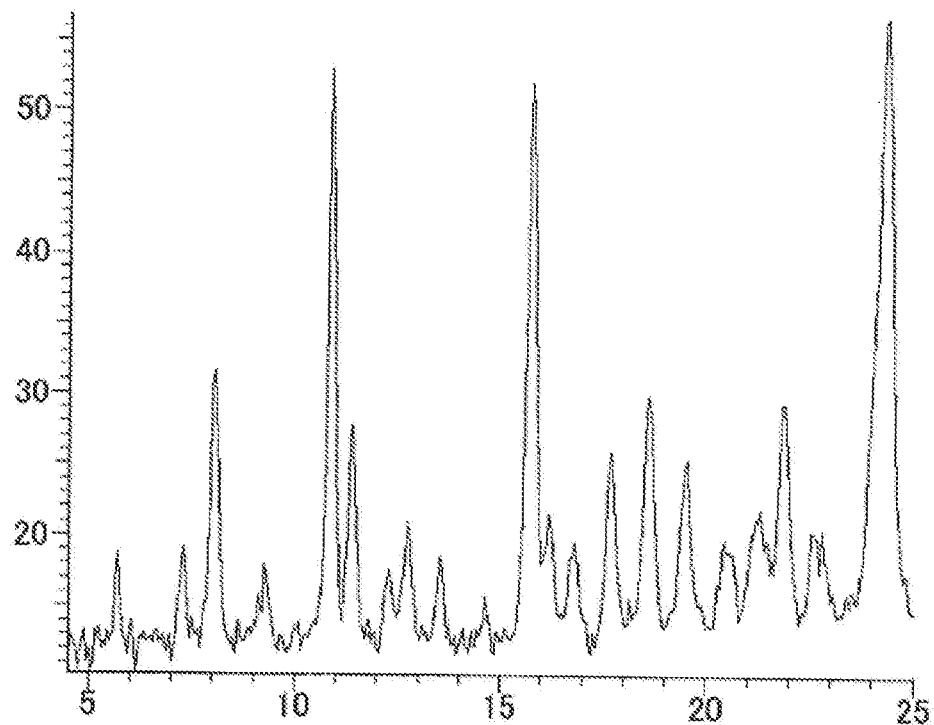
FIG. 14 is a powder X-ray diffraction spectrum chart showing N-{5-[(6,7-dimethoxy-4-quinolinyl)oxy]-2-pyridinyl}-2,5-dioxo-1-phenyl-1,2,5,6,7,8-hexahydro-3-quinolinecarboxamide hydrochloride (C-type crystal) (in FIG. 14, the ordinate shows strength (counts) and the abscissa shows 2θ (°)).
Figure 15:
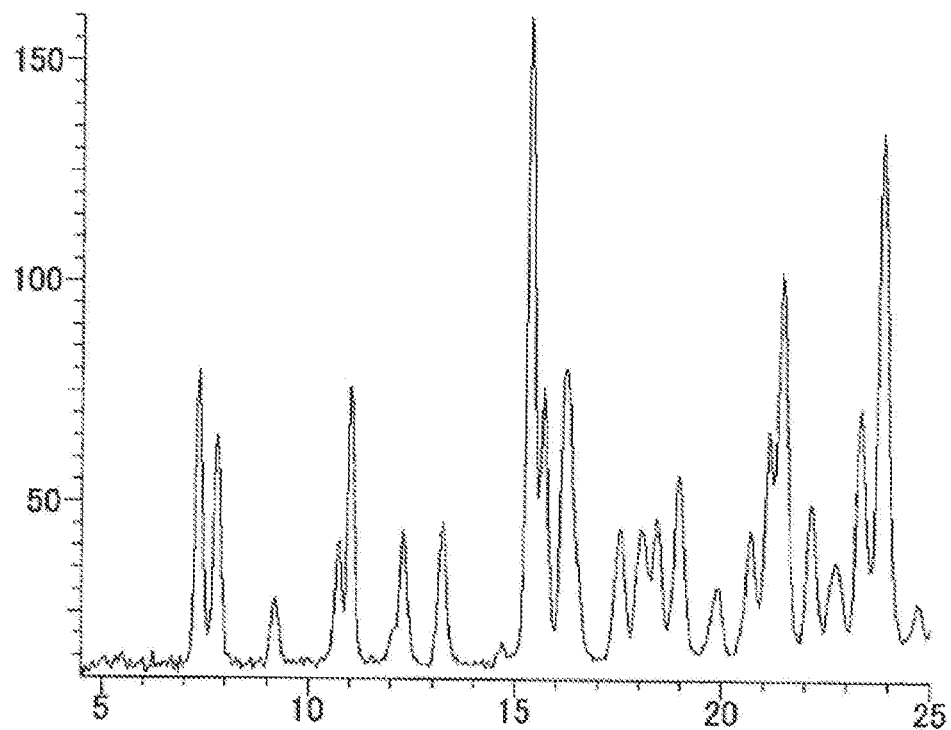
FIG. 15 is a powder X-ray diffraction spectrum chart showing N-{5-[(6,7-dimethoxy-4-quinolinyl)oxy]-2-pyridinyl}-2,5-dioxo-1-phenyl-1,2,5,6,7,8-hexahydro-3-quinolinecarboxamide methanesulfonate (A-type crystal) (in FIG. 15, the ordinate shows strength (counts) and the abscissa shows 2θ (°)).
Figure 16:
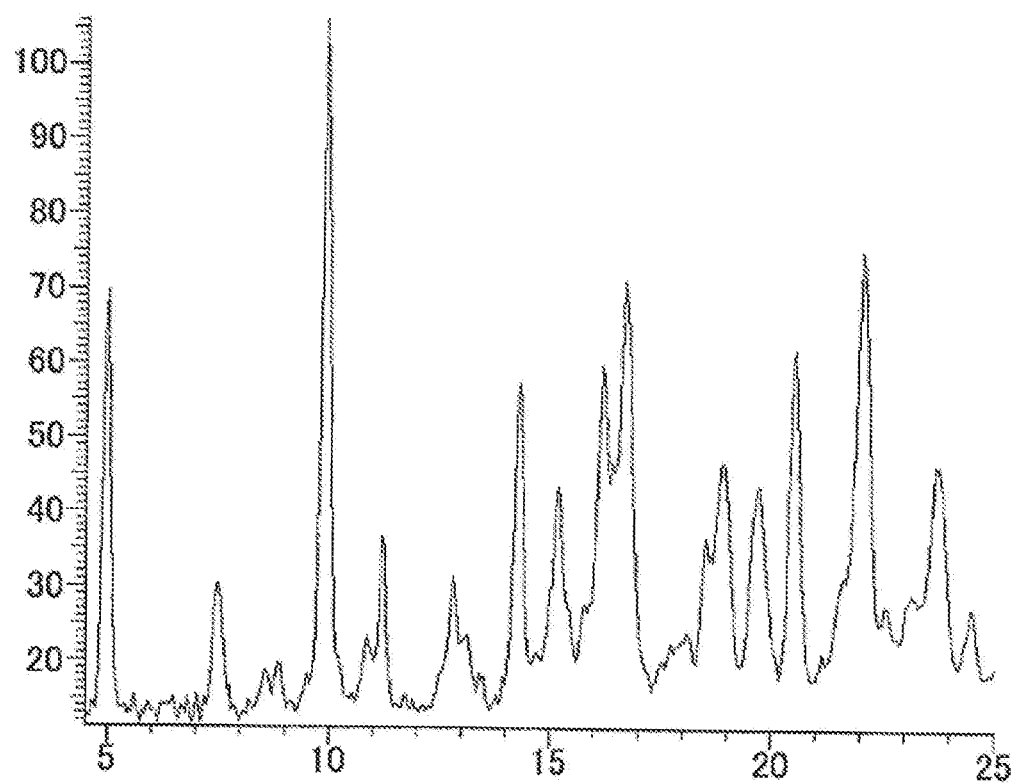
FIG. 16 is a powder X-ray diffraction spectrum chart showing N-{5-[(6,7-dimethoxy-4-quinolinyl)oxy]-2-pyridinyl}-2,5-dioxo-1-phenyl-1,2,5,6,7,8-hexahydro-3-quinolinecarboxamide p-toluenesulfonate (C-type crystal) (in FIG. 16, the ordinate shows strength (counts) and the abscissa shows 2θ (°)).
Figure 17:
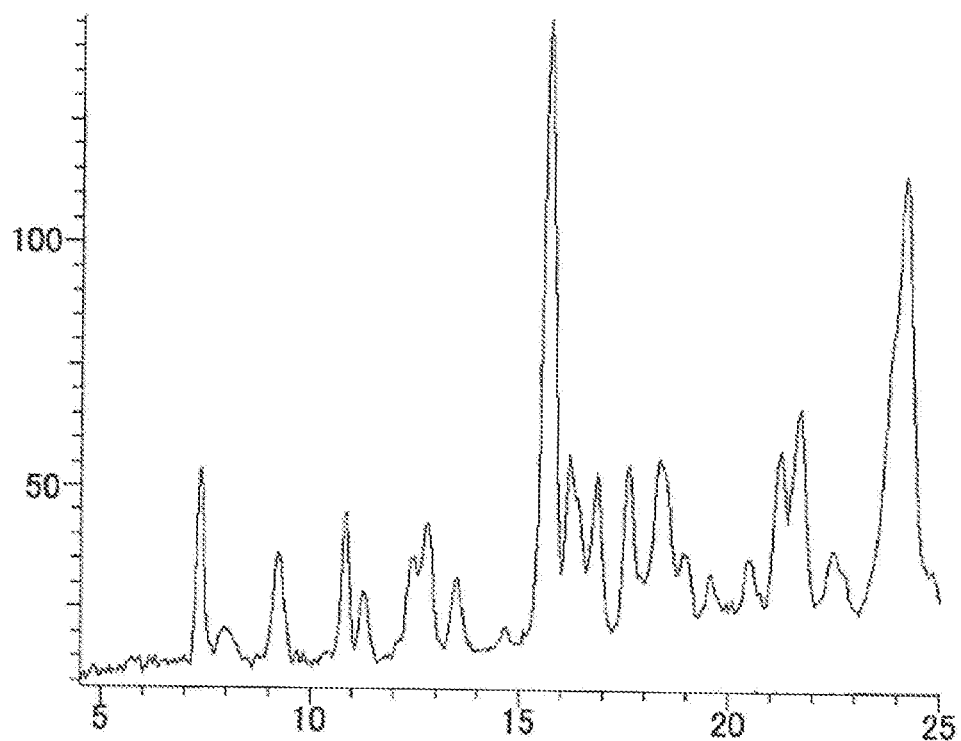
FIG. 17 is a powder X-ray diffraction spectrum chart showing N-{5-[(6,7-dimethoxy-4-quinolinyl)oxy]-2-pyridinyl}-2,5-dioxo-1-phenyl-1,2,5,6,7,8-hexahydro-3-quinolinecarboxamide sulfate (A-type crystal) (in FIG. 17, the ordinate shows strength (counts) and the abscissa shows 2θ (°)).

As shown in FIG. 4, the C-crystal of the compound A showed endothermic peaks with respect to fusion, shown by the onset temperature of about 160.3° C. and the peak temperature of about 175.8° C., respectively.

A method for producing various acid addition salts of compounds A will be described later in Examples, but it is found that since the acid addition salts other than the compounds of the present invention have crystal polymorphisms and that control of the polymorphisms of the crystal is difficult.

In the present invention, crystal forms of the compound A or various acid addition salts of the compound A are specified by physicochemical data described in the present application, but each spectral data should not be strictly interpreted as they vary somewhat in natures.

For example, in the powder X-ray diffraction spectrum data, the diffraction angle (2θ) and the overall pattern are important for recognition of the identity of the crystal because of its nature, and the relative intensity may somewhat vary depending on the direction of crystal growth, the size of the particles, and the measurement conditions.

Furthermore, also in the DSC data, the overall pattern is important for recognition of the identity of the crystal, and may vary depending on the measurement conditions.

Therefore, in the compounds of the present invention, compounds in which the powder X-ray diffraction spectrum or the DSC and patterns are similar as a whole, are included in the compound of the present invention.

In the present application, it is meant that the descriptions of the diffraction angle (2θ (°)) in the powder X-ray diffraction pattern and the onset temperature (° C.) of the endothermic peak in the DSC analysis include an error range normally allowed in the data measurement method, and means approximately the diffraction angle and the onset value of endothermic peak. For example, the term "about" to diffraction angle (2θ (°)) in the powder X-ray diffraction is ±0.2° in one aspect, and ±0.1° in another aspect. The "about" to the onset temperature (° C.) of the endothermic peak in the DSC analysis is ±2° C. in one aspect.

In one exemplary embodiment of the present invention, each of the crystal forms of the compound A, or various acid addition salts of the compound A is substantially pure. Referring to "substantially pure" means that a specific crystal form occupies at least 50% in the existing compound. Furthermore, in another exemplary embodiment, each crystal form occupies at least 75%, at least 85%, at least 90%, at least 95% or about 94% to 98% in the existing compound A.

In the present invention, the compound A, or various acid addition salts of the compound A can be produced by, for example, methods of the below-mentioned Examples, and methods same as such methods. Note here that in recrystallization, a seed crystal may be used or not may be used.

The compound of the present invention may be able to be converted into a solvate. The solvate has preferably low toxicity and water-solubility. Examples of the appropriate solvate include solvates with water, an alcohol solvent (for example, ethanol), and the like.

[Toxicity]

The toxicity of the compound of the present invention is sufficiently low, and the compound can be safely used as pharmaceuticals.

[Application to Pharmaceuticals]

Since the compound of the present invention has an Axl inhibiting activity, it can be used as an agent for preventing and/or treating an Axl-related disease in mammals, particularly, in human.

In the present invention, examples of the Axl-related diseases include cancer, kidney diseases, immune system disease, and circulatory system disease.

In the present invention, examples of the cancer include leukemia (for example, acute myeloid leukemia, chronic myeloid leukemia, acute lymphatic leukemia, and chronic lymphatic leukemia), malignant lymphoma (Hodgkin lymphoma and non-Hodgkin lymphoma (for example, adult T-cell leukemia, follicular lymphoma, and diffuse large B-cell malignant lymphoma)), multiple myeloma, myelodysplasia syndrome, head and neck cancer, esophageal cancer, esophageal adenocarcinoma, stomach cancer, large intestine cancer, colon cancer, rectum cancer, liver cancer (for example, hepatocellular cancer), gallbladder cancer and bile duct cancer, biliary tract cancer, pancreatic cancer, thyroid cancer, lung cancer (for example, non-small cell lung cancer (for example, squamous epithelium non-small cell lung cancer, non-squamous epithelium non-small cell lung cancer), and small-cell lung cancer), breast cancer, ovarian cancer (for example, serous ovarian cancer), cervical cancer, uterine body cancer, endometrial cancer, vaginal cancer, vulvar cancer, renal cancer (for example, renal cell carcinoma), urothelial carcinoma (for example, urinary bladder cancer, and upper urinary tract cancer), prostate cancer, testicular tumor (for example, germ cell tumor), bone and soft tissue sarcoma, skin cancer (for example, uveal malignant melanoma, malignant melanoma (melanoma), and Merkel cell cancer), glioma, brain tumor (for example, glioblastoma), pleural mesothelioma, and unknown primary cancer.

In the present invention, examples of the kidney diseases include glomerular nephritis, chronic nephritis, IgA nephritis, sequential (secondary) nephritis, nephrosis nephritis, acute renal failure, chronic renal failure, diabetic nephropathy, gouty nephropathy, interstitial nephritis, and nephropyelitis.

In the present invention, examples of the immune system disease include psoriasis, and rheumatoid arthritis.

In the present invention, examples of the circulatory system disease include atherosclerosis and thrombosis.

Furthermore, since the compound of the present invention has an Axl inhibiting activity, it can be used as a metastasis-suppressing agent to tumor cells.

The compound of the present invention may be administered as a combination drug in combination with other drugs in order to accomplish the following purposes:
1) to supplement and/or enhance the preventive and/or therapeutic effect of the compound;
2) to improve the kinetics and absorption, and to reduce the dose of the compound; and/or
3) to eliminate the side effects of the compound.

A combination drug of the compound of the present invention and other drugs may be administered in the form of a compounding agent including these components mixed into one formulation, or may be administered in separate formulations. Administration as separate formulations includes simultaneous administration and administration at different times. In the administration at different times, the compound of the present invention may be administered before the other drug. Alternatively, the other drug may be administered before the compound of the present invention. The method for the administration of these drugs may be the same as each other or different from each other.

Diseases on which the preventive and/or therapeutic effect of the above-mentioned combination drug works are not particularly limited but may be those in which the preventive and/or therapeutic effect of the compound of the present invention is supplemented and/or enhanced.

The other drugs for supplementing and/or enhancing the preventive and/or therapeutic effect of the compound of the present invention against cancer include, for example, alkylating agents, antimetabolites, anticancer antibiotics, plant alkaloids, hormones, platinum compounds, immune checkpoint inhibitors, anti-CD20 antibodies, anti-CD52 antibodies, G-CSF formulations, acute promyelocytic leukemia differentiation-inducing agents, kinase inhibitors, topoisomerase inhibitors, aromatase inhibitors, and other anticancer drugs.

The other drug for supplementing and/or enhancing the preventive and/or therapeutic effect of the compound of the present invention against kidney diseases include, for example, steroids, immunosuppressants, angiotensin II antagonistic drugs, angiotensin-converting enzyme inhibitors, antiplatelet drugs, and anticoagulant drugs.

The other drugs for supplementing and/or enhancing the preventive and/or therapeutic effect of the compound of the present invention against immune system diseases include, for example, immunosuppressants; steroids; disease-modifying anti-rheumatic drugs; prostaglandins; prostaglandin synthase inhibitors; phosphodiesterase inhibitors; metalloprotease inhibitors; anti-cytokine protein formulations such as anti-TNF-α formulations, anti-IL-1 formulations, and anti-IL-6 formulation; cytokine inhibitors; and nonsteroidal anti-inflammatory agents.

Examples of the other drugs for supplementing and/or enhancing the preventive and/or therapeutic effect of the compound of the present invention against circulatory system diseases include antiplatelet drugs, angiotensin II antagonistic drugs, angiotensin-converting enzyme inhibitors, HMG-CoA reductase inhibitors, and thiazolidine derivatives.

Examples of the alkylating agents include nitrogen mustard N-oxide hydrochloride, cyclophosphamide, ifosfamide, melphalan, thiotepa, carboquone, busulfan, nimustine hydrochloride, dacarbazine, ranimustine, carmustine, chlorambucil, bendamustine, and mechlorethamine.

Examples of the antimetabolites include methotrexate, mercaptopurine, 6-mercaptopurine riboside, fluorouracil, tegafiur, tegafur uracil, carmofur, doxifluridine, cytarabine, enocitabine, tegafur gimestat otastat potassium, gemcitabine hydrochloride, cytarabine ocfosfate, procarbazine hydrochloride, hydroxycarbamide, and the like.

Examples of the anticancer antibiotics include actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, zinostatin stimalamer, Gemtuzumab Ozogamicin, and the like.

Examples of the plant alkaloid drug include vinblastine sulfate, vincristine sulfate, vindesine sulfate, irinotecan hydrochloride, etoposide, flutamide, vinorelbine tartrate, docetaxel hydrate, paclitaxel, and the like.

Examples of the hormones include estramustine phosphate sodium, mepitiostane, 30 epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, aminoglutethimide, androgen bicalutamide, fulvestrant, and the like.

Examples of the platinum compounds include carboplatin, cisplatin, nedaplatin, and oxaliplatin, and the like.

The immune checkpoint inhibitor is a substance that inhibits the function of an immunization checkpoint molecule. The immune checkpoint inhibitor is not particularly limited as long as the substance can suppress the function (signal) of the immunization checkpoint molecule.

The immune checkpoint inhibitor is preferably an inhibitor of a human immunization checkpoint molecule, and further preferably a neutralization antibody against a human immunization checkpoint molecule.

Examples of the immune checkpoint inhibitor include an inhibitor of the immunization checkpoint molecule selected from the group consisting of CTLA-4, PD-1, PD-L, PD-L2, LAG-3, TIM3, BTLA, B7H3, B7H4, 2B4, CD160, A2aR, KIR, VISTA, and TIGIT. The followings are examples of the immune checkpoint inhibitor, but the immune checkpoint inhibitors are not particularly limited thereto.

Examples of the immune checkpoint inhibitor include an anti-CTLA-4 antibody (for example, Ipilimumab (YERVOY (registered trademark)), Tremelimumab, AGEN-1884), anti-PD-1 antibody (for example, nivolumab (OPDIVO (registered trademark)), REGN-2810, Pembrolizumab (KEYTRUDA (registered trademark)), PDR-001, BGB-A317, AMP-514 (MEDI0680), BCD-100, IBI-308, JS-001, PF-06801591, and TSR-042), an anti-PD-L1 antibody (for example, Atezolizumab (RG7446 and MPDL3280A), Avelumab (PF-06834635 and MSB0010718C), Durvalumab (MEDI4736), BMS-936559, CA-170, and LY-3300054), anti-PD-L2 antibody (for example, rHIgM12B7), PD-L1 fusion protein, PD-L2 fusion protein (for example, AMP-224), an anti-Tim-3 antibody (for example, MBG453), an anti-LAG-3 antibody (for example, BMS-986016, and LAG525), and an anti-KIR antibody (for example, Lirilumab). Furthermore, antibodies including heavy chain and light chain complementarity determining regions (CDRs) or variable region (VR) of the above-mentioned known antibodies are also one embodiment of the immune checkpoint inhibitor. Examples of further embodiment of the anti-PD-1 antibody include an antibody including heavy chain and light chain complementarity determining regions (CDRs) or variable region (VR) of nivolumab.

Examples of the anti-CD20 antibodies include rituximab, ibritumomab, ibritumomab tiuxetan, and ocrelizumab.

Examples of the anti-CD52 antibodies include alemtuzumab.

Examples of the G-CSF formulation include pegfilgrastim, filgrastim, lenograstim, and nartograstim.

Examples of the differentiation-inducing agent for acute promyelocytic leukemia include tamibarotene, tretinoin, and arsenic trioxide formulations.

Examples of the kinase inhibitors include EGFR inhibitors including erlotinib hydrochloride, gefitinib, cetuximab, and panitumumab; HER2 inhibitors including lapatinib and trastuzumab; BCR-ABL inhibitors including imatinib, dasatinib, and nilotinib; multikinase inhibitors including sunitinib, vandetanib, crizotinib, and sorafenib.

Examples of the topoisomerase inhibitor include topotecan, teniposide, irinotecan, and sobuzoxane.

Examples of the aromatase inhibitor include exemestane.

Examples of the other anticancer agents include L-asparaginase, octreotide acetate, porfimer sodium, mitoxantrone acetate, aceglatone, ubenimex, eribulin mesilate, cladribine, krestin, bexarotene, denileukin diftitox, temozolomide, nelarabine, fludarabine, bevacizumab, pemetrexed, pentostatin, bortezomib, lenalidomide, and calcium folinate.

Examples of the immunosuppressant include azathioprine, ascomycin, everolimus, salazosulfapyridine, cyclosporine, cyclophosphamide, sirolimus, tacrolimus, bucillamine, methotrexate, and leflunomide.

Examples of the steroid include amcinonide, hydrocortisone sodium succinate, prednisolone sodium succinate, methylprednisolone sodium succinate, ciclesonide, difluprednate, betamethasone propionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfate, mometasone furoate, fluocinonide, fluocinolone acetonide, fludroxycortide, flunisolide, prednisolone, alclometasone propionate, clobetasol propionate, dexamethasone propionate, deprodone propionate, fluticasone propionate, beclometasone propionate, betamethasone, methylprednisolone, methylprednisolone suleptanate, methylprednisolone sodium succinate, dexamethasone sodium phosphate, hydrocortisone sodium phosphate, prednisolone sodium phosphate, diflucortolone valerate, dexamethasone valerate, betamethasone valerate, prednisolone valerate acetate, cortisone acetate, diflorasone acetate, dexamethasone acetate, triamcinolone acetate, paramethason acetate, halopredone acetate, fludrocortisone acetate, prednisolone acetate, methylprednisolone acetate, clobetasone butyrate, hydrocortisone butyrate, hydrocortisone butyrate propionate, and betamethasone butyrate propionate.

Examples of the angiotensin II antagonistic drug include Losartan, candesartan, valsartan, irbesartan, olmesartan, telmisartan, and the like.

Examples of the angiotensin-converting enzyme inhibitor include alacepril, imidapril hydrochloride, quinapril hydrochloride, temocapril hydrochloride, delapril hydrochloride, benazepril hydrochloride, captopril, trandolapril, perindopril erbumine, enalapril maleate, lisinopril, and the like.

Examples of the antiplatelet drugs include dipyridamole, and dilazep hydrochloride hydrate.

Examples of the anticoagulant drugs include warfarin and heparin.

Examples of the disease-modifying anti-rheumatic drugs include D-penicillamine, actarit, auranofin, salazosulfapyridine, hydroxychloroquine, bucillamine, methotrexate, leflunomide, lobenzarit sodium, aurothioglucose, and sodium aurothiomaleate.

Examples of the prostaglandins (hereinafter, abbreviated as "PG") include PGE1 formulations (examples: alprostadil alfadex, alprostadil), PGI2 formulations (example: beraprost sodium), PG receptor agonists, and PG receptor antagonists. Examples of the PG receptor include PGE receptors (EP1, EP2, EP3, and EP4), PGD receptors (DP, and CRTH2), PGF receptors (FP), PGI2 receptors (IP), and TX receptors (TP).

Examples of the prostaglandin synthase inhibitor include salazosulfapyridine, mesalazine, olsalazine, 4-aminosalicylic acid, JTE-522, auranofin, carprofen, difenpiramide, flunoxaprofen, flurbiprofen, indometacin, ketoprofen, lornoxicam, loxoprofen, meloxicam, oxaprozin, parsalmide, naproxen, piroxicam, piroxicam cinnamate, zaltoprofen, and pranoprofen.

Examples of the phosphodiesterase inhibitor include rolipram, cilomilast, Bay19-8004, NIK-616, roflumilast (BY-217), cipamfylline (BRL-61063), atizoram (CP-80633), ONO-6126, SCH-351591, YM-976, V-11294A, PD-168787, D-4396, and IC-485.

Examples of the anti-TNF-α formulation include anti-TNF-α antibodies, soluble TNF-α receptor, anti-TNF-α receptor antibodies, and soluble TNF-α binding protein, and particularly infliximab and etanercept.

Examples of the anti-IL-1 formulation include anti-IL-1 antibodies, soluble IL-1 receptor, anti-IL-1Ra antibodies and/or anti-IL-1 receptor antibodies and particularly anakinra.

Examples of the anti-IL-6 formulation include anti-IL-6 antibodies, soluble IL-6 receptor, and anti-IL-6 receptor antibodies, and particularly tocilizumab.

Examples of the cytokine inhibitor include suplatast tosylate, T-614, SR-31747, and sonatimod.

Examples of the HMG-CoA reductase inhibitor include atorvastatin, fluvastatin, lovastatin, pitavastatin, pravastatin, rosuvastatin, and simvastatin.

Examples of the thiazolidine derivative include pioglitazone, ciglitazone, rosiglitazone, and troglitazone.

Furthermore, the combination drugs to be combined with a compound of the present invention includes not only ones discovered to date, but also ones that may be discovered in the future.

The compound of the present invention, after formulated as an appropriate pharmaceutical composition together with a pharmaceutically acceptable carrier, is usually administered systemically or locally, by oral or parenteral administration. Examples of oral agents include liquid medicines for internal use (for example, elixirs, syrups, pharmaceutically acceptable water-based agents, suspensions, and emulsions), and solid medicine for internal use (for example, tablets (including sublingual tablets and/orally disintegrating tablets), pills, capsules (including hard capsules, soft capsules, gelatin capsules, and microcapsules), powders, granules, and lozenges). Examples of parenteral agents include liquid medicines (for example, injection agents (for example, subcutaneous injection agents, intravenous injection agents, intramuscular injection agents, intraperitoneal injection agents, and drip agents), eye drops (for example, aqueous eye drops (aqueous eye drops, aqueous eye drop suspensions, viscous eye drops, and solubilized eye drops, etc.), and nonaqueous eye drops (nonaqueous eye drops and nonaqueous eye drop suspensions), and the like), agents for external use (for example, ointments (ophthalmic ointments, and the like)), and ear-drops, and the like. These formulations may be controlled release agents such as rapid release formulations, sustained release formulations, and the like. These formulations can be produced by well-known methods, for example, by the methods described in The Japanese Pharmacopoeia.

Liquid medicines for internal use as the oral agent can be produced by, for example, dissolving or suspending the compound of the present invention in a generally used diluent (for example, purified water, ethanol, or mixture liquid thereof, or the like). The liquid medicine may include a wetting agent, a suspension agent, a sweetening agent, a flavoring material, an aromatic substance, a preservative, a buffer agent, and the like.

Solid medicines for internal use as the oral agent are formulated by, for example, mixing the compound of the present invention with, for example, a vehicle (for example, lactose, mannitol, glucose, microcrystalline cellulose, and starch), a binder (for example, hydroxypropyl cellulose, polyvinylpyrrolidone, and magnesium metasilicate aluminate), a disintegrant (for example, sodium carboxymethylcellulose), a lubricant (for example, magnesium stearate), a stabilizer, a dissolution adjuvant (for example, glutamic acid and aspartic acid), and the like, and formulating according to standard methods. As necessary, coating may be carried out with a coating agent (for example, sugar, gelatin, hydroxypropyl cellulose, and hydroxypropyl methyl cellulose phthalate), and coating of two or more layers may be employed.

Agents for external use as parenteral agents are produced by well-known methods or generally used prescriptions. For example, an ointment may be produced by trituration or melting of the compound of the present invention base material. The ointment base material is selected from well-known material or generally used material. For example, a single material or a mixture of two or more of materials are selected from higher fatty acids or higher fatty acid esters (for example, adipic acid, myristic acid, palmitic acid, stearic acid, oleic acid, adipate esters, myristate esters, palmitate esters, stearate esters, and oleate esters), waxes (for example, beeswax, spermaceti, and ceresin), surfactants (for example, polyoxyethylene alkyl ether phosphate esters), higher alcohols (for example, cetanol, stearyl alcohol, and cetostearyl alcohol), silicone oils (for example, dimethylpolysiloxane), hydrocarbons (for example, hydrophilic petrolatum, white petrolatum, purified lanolin, and liquid paraffin), glycols (for example, ethylene glycol, diethylene glycol, propylene glycol, polyethylene glycol, and macrogol), plant oils (for example, castor oil, olive oil, sesame oil, and turpentine oil), animal oils (for example, mink oil, egg yolk oil, squalane, and squalene), water, absorption promoters, and anti-irritants. Furthermore, a humectant, preservative, stabilizer, antioxidant, fragrance, and the like, may be included.

The injection agents as parenteral agents include solutions, suspensions, emulsions and solid injection agents to be dissolved or suspended in a solvent before use. The injection agent is used by, for example, dissolving, suspending or emulsifying the compound of the present invention in a solvent. Examples of the solvent include distilled water for injection, physiological saline, vegetable oils, alcohols such as propylene glycol, polyethylene glycol, ethanol, and mixtures thereof. Furthermore, the injection agent may contain a stabilizer, a dissolution aid (glutamic acid, aspartic acid, and Polysorbate 80 (registered trademark), etc.), a suspending agent, an emulsifying agent, a soothing agent, a buffer, a preservative, and the like. Such an injection agent is produced by sterilizing at the final step or employing an aseptic process. Furthermore, it is also possible to employ an aseptic solid product such as a freeze-dried product produced and sterilized or dissolved in aseptic distilled water for injection or other solvent before use.

The dose of the compound of the present invention can be appropriately selected depending on conditions, ages, formulations, and the like. An oral agent may be administered preferably in the dose of 1 to 100 mg, and more preferably 5 to 30 mg once to several times per day (for example, one to three times). Alternatively, an agent may be administered in a range of 50 µg to 500 mg for one time to several times by parenteral administration or sustainably administered in a range from one hour to 24 hours for one day.

Needless to say, as mentioned above, the dose to be administered varies dependent on various conditions. Therefore, dose lower than the ranges specified above may be sufficient in some cases, and dose higher than the ranges specified above are needed in some cases.

EXAMPLES

Hereinafter, the present invention is described in detail with reference to Examples mentioned below, but the present invention is not limited thereto.

Solvents given in parentheses shown in chromatographic separation and TLC each indicate the elution solvent or the developing solvent used, and the ratio is expressed in ratio by volume.

The NMR data are data of $^1$H-NMR data unless otherwise noted.

The description in a parenthesis in the NMR data shows a solvent used for measurement.

Name of the compounds used in this specification are named by using ACD/Name (registered trademark) manufactured by Advanced Chemistry Development Inc., which is generally a computer program for naming compounds according to the regulation of IUPAC, or named according to the naming method of IUPAC.

Example 1

4-[(6-chloro-3-pyridinyl)oxy]-6,7-dimethoxy quinoline

Under a stream of nitrogen, a chlorobenzene solution (9 mL) of 4-chloro-6,7-dimethoxy quinoline (1.00 g) (CAS registration No.: 35654-56-9), 6-chloropyridine-3-ol (0.65 g), and triethylamine (11.3 mL) were placed in a 100 mL four-necked flask, followed by being stirred at a bath temperature (140° C.) for five days. The resulting solution was allowed to cool to room temperature, water and ethyl acetate were added thereto, and the solution was separated. The water layer was extracted again with ethyl acetate. The combined organic layer was washed with a saturated saline solution, and dried over anhydrous sodium sulfate. A solvent was removed by evaporation under reduced pressure. The obtained residue was purified by silica gel column chromatography (hexane:ethyl acetate=1:8) to obtain the title compound (1.16 g) having the following physical property values.

TLC: Rf 0.22 (hexane:ethyl acetate=1:3);
$^1$H-NMR (DMSO-d$_6$): δ 8.52, 8.48, 7.87-7.85, 7.66, 7.49, 7.43, 6.65, 3.95, 3.93.

Example 2

5-[(6,7-dimethoxy-4-quinolinyl)oxy]-2-pyridinamine

Under a stream of nitrogen, a tetrahydrofuran (THF) solution (18 mL) of the compound (1.15 g) produced in Example 1, 1.0 mol/L lithium bis(trimethylsilyl)amide (LHDMS) (5.45 mL), tris(dibenzylideneacetone)dipalladium(0) chloroform complex (0.19 g), and 2-dicyclohexylphosphino-2',6'-dimethoxybiphenyl (0.15 g) were placed in a 200-mL four-necked flask, followed by being stirred at a bath temperature (80° C.) for 16.5 hours. Furthermore, 6 mol/L hydrochloric acid (10 mL) was added thereto, followed by being stirred at a bath temperature (80° C.) for two hours. The mixture was allowed to cool to room temperature, then a saturated aqueous sodium hydrogen bicarbonate solution and ethyl acetate were added, and the resulting solution was separated. The water layer was extracted again with ethyl acetate. The combined organic layer was washed with a saturated saline solution, and then dried over anhydrous sodium sulfate. A solvent was removed by evaporation under reduced pressure. The resulting residue was purified by silica gel column chromatography (ethyl acetate→ethyl acetate:methanol=9:1) to obtain the title compound (0.80 g) having the following physical property values.

TLC: Rf 0.51 (ethyl acetate:methanol=4:1);
$^1$H-NMR (DMSO-d$_6$): δ 8.45, 7.89, 7.51, 7.38-7.36, 6.56, 6.42, 6.05, 3.94.

Example 3

Ethyl 2,5-dioxo-5,6,7,8-tetrahydro-2H-chromene-3-carboxylate

At room temperature, 1,3-cyclohexanedione (CAS registration No: 504-02-9) (13.25 g) was dissolved in N,N-dimethylformamide (DMF) (200 mL), and tert-butoxypotassium (13.26 g), ethyl (E)-2-cyano-3-ethoxy-2-propanoate (CAS registration No: 94-05-3) (20.00 g) were added, followed by being stirred for 21 hours. The reaction solution was diluted with ethyl acetate, and 2 mol/L of hydrochloric acid aqueous solution was added and the resultant product was stirred. Furthermore, ethyl acetate and water were added to extract an organic layer. The resultant product was washed with saturated saline and dried over anhydrous sodium sulfate, and a solvent was removed by evaporation under reduced pressure to obtain the titled compound (23.62 g) having the following physical property value.

TLC: Rf 0.35 (hexane:ethyl acetate=1:1);
$^1$H-NMR (CDCl$_3$): δ 1.37, 2.19, 2.61, 2.92, 4.36, 8.63.

Example 4

2,5-dioxo-1-phenyl-1,2,5,6,7,8-hexahydro-3-quinoline carboxylic acid

At room temperature, the compound (10.00 g) produced in Example 3 was dissolved in ethanol (200 mL), aniline (3.94 g) was added thereto, and the resultant product was stirred for 6 hours. Solids precipitating from the reaction solution were collected by filtration using a Kiriyama funnel and washed with ethanol. The obtained residues were dried under reduced pressure at 60° C. The titled compound (4.01 g) having the following physical property value was obtained.

TLC: Rf 0.37 (dichloromethane:methanol=9:1);
$^1$H-NMR (CDCl$_3$): δ 2.11, 2.60, 7.25, 7.63, 9.21.

Example 5

N-{5-[(6,7-dimethoxy-4-quinolinyl)oxy]-2-pyridinyl}-2,5-dioxo-1-phenyl-1,2,5,6,7,8-hexahydro-3-quinolinecarboxamide (Compound A)

[Chem. 9]

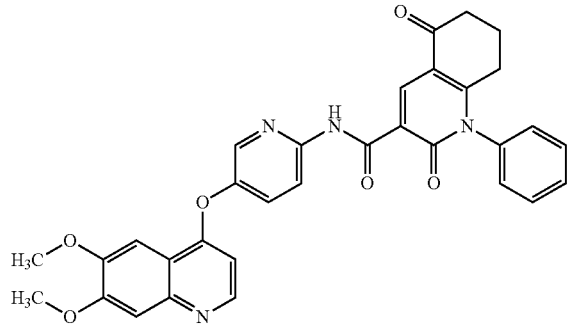

At room temperature, the compound (105 mg) produced in Example 4, and O-(7-aza-1-benzotriazolyl)-N,N,N',N'-tetramethyl uronium hexafluorophosphate (HATU) (192 mg) were dissolved in DMF (2 mL), and diisopropyl ethylamine (DIPEA) (0.17 mL), and the compound (100 mg) produced in Example 2 were added thereto, and the resultant product was stirred for 21 hours. The solvent was removed by evaporation under reduced pressure, and the obtained residues were purified by silica gel chromatography (hexane:ethyl acetate=30:70→0:100→ethyl acetate:methanol=70:30) to obtain the titled compound (116 mg) having the following physical property value.

TLC: Rf 0.76 (ethyl acetate:methanol=5:1);
$^1$H-NMR (CDCl$_3$): δ 2.13, 2.60, 4.05, 6.44, 7.25, 7.42, 7.53, 7.63, 8.22, 8.48, 8.51, 9.32, 11.93.

Example 5 (1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide (C-Type Crystal)

The compound A (10 mg) produced by the similar method as in Example 5 was placed in 1.5 mL-vial, 17% hydrated acetonitrile (0.9 mL) was added thereto, and the resultant product was stirred at 60 to 80° C. The reaction solution was cooled to room temperature, and the obtained crystals were collected by filtration and dried overnight at room temperature to obtain the titled compound (4 mg) as a white crystal.

Example 5 (2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide (D-Type Crystal)

The compound A (60 mg) produced by the method corresponding to Example 5 was placed in 10-mL test tube, and acetonitrile (3 mL) was added thereto. The obtained product was stirred at 60 to 80° C. The reaction solution was cooled to room temperature, and the obtained crystals were collected by filtration, and dried overnight at room temperature to obtain the titled compound (15 mg) as a white crystal.

Example 5 (3)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide (E-Type Crystal)

Figure 18:
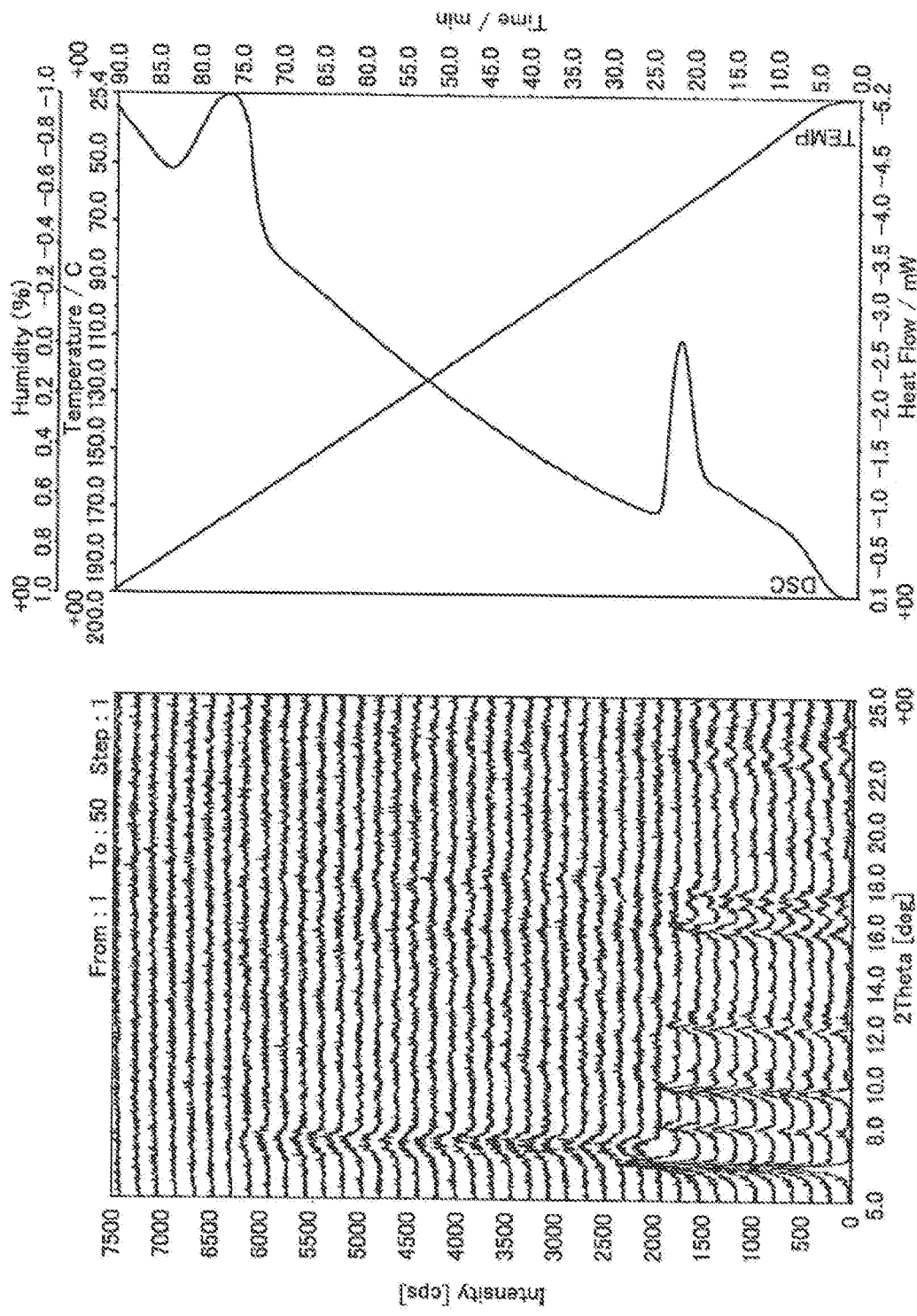
FIG. 18 is a powder X-ray-DSC spectrum chart showing N-{5-[(6,7-dimethoxy-4-quinolinyl)oxy]-2-pyridinyl}-2,5-dioxo-1-phenyl-1,2,5,6,7,8-hexahydro-3-quinolinecarboxamide (E-type crystal).

The compound A (10 mg) produced in Example 5 was placed in 1.5 mL-vial, 33% hydrated acetone (0.75 mL) was added thereto, followed by being stirred at 45 to 55° C. The reaction solution was cooled to room temperature, and the obtained crystals were collected by filtration and dried overnight at room temperature to obtain the titled compound (3 mg) as a white crystal. From the results of FIG. 18, around 55 to 70° C., according to the change in crystalline structure, endothermic peak according to dehydration and patterns in the X-ray diffraction spectrum chart, were observed. The compound of this Example was suggested to be a hydrate of the compound A.

Example 5 (4)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide (F-Type Crystal)

To the compound A (23.7 g) produced by the same procedure as in Example 5, acetone (80 mL) was added. The obtained product was stirred at 40° C. for one hour, and subjected to filtration to collect powder. To the collected powder, methanol (120 mL) was added. The resultant product was stirred at 60° C. for one hour. After cooling, the obtained crystals were collected by filtration overnight at 80° C. to obtain the titled compound (21.4 g) as a white crystal.

Example 5 (5)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide (G-Type Crystal)

The compound (10 mg) produced in Example 5(4) was placed in 1.5 mL-vial, 33% hydrated acetonitrile (0.75 mL) was added thereto, followed by being stirred at 45 to 55° C. The reaction solution was cooled to room temperature, and the obtained crystals were collected by filtration and dried overnight at room temperature to obtain the titled compound (7 mg) as a white crystal.

Example 5 (6)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide (H-Type Crystal)

The compound (60 mg) produced in Example 5(4) was placed in 10-mL test tube, acetonitrile (3 mL) was added thereto, followed by being stirred at 60 to 80° C. The reaction solution was cooled to room temperature, and the obtained crystals were collected by filtration and dried overnight at room temperature to obtain the titled compound (40 mg) as a white crystal.

Example 6

N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate Into a 50-mL flask, the compound A (9 g) produced in Example 5 was placed, and acetone (270 mL) was added thereto, followed by being stirred at 40 to 50° C. Ethane sulfonic acid (1.31 mL) was added to this reaction solution, and the obtained crystals were collected by filtration and dried overnight at 60° C. Thus, the titled compound (11 g) having the following physical property value was obtained as a white crystal.
LC-MS: 563 (M+H)$^+$;
$^1$H-NMR (DMSO-d$_6$): δ 1.04, 1.93-2.05, 2.36, 2.45-2.59, 4.02, 4.03, 7.01, 7.43-7.50, 7.53, 7.57-7.69, 7.74, 7.99, 8.44-8.53, 8.81, 8.98, 12.04.

Example 7

N-{5-[(6,7-dimethoxy-4-quinolinyl)oxy]-2-pyridinyl}-2,5-dioxo-1-phenyl-1,2,5,6,7,8-hexahydro-3-quinolinecarboxamide hydrochloride (C-Type Crystal)

The compound A (0.5 g) produced in Example 5 was placed in 50-mL flask, acetonitrile (80 mL) was added thereto, followed by being stirred at 15 to 25° C. To this reaction solution, 2 mol/L hydrochloric acid aqueous solution (0.93 mL) was added, and the mixture was stirred. The solvent was removed by evaporation under reduced pressure, and dried overnight at 75° C. to obtain the titled compound (0.53 g) having the following physical property value as a white crystal.
LC-MS: 563 (M+H)$^+$;
$^1$H-NMR (DMSO-d$_6$): δ 1.93-2.06, 2.46-2.55, 4.02, 4.04, 6.99, 7.44-7.50, 7.57, 7.58-7.69, 7.75, 8.00, 8.45-8.53, 8.81, 8.99, 12.05.

Example 7(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide hydrochloride The compound produced in Example 5 was added to a solvent (for example, dioxane) or a mixed solvent (for example, a mixed solvent of acetonitrile and water) as well as a hydrochloric acid aqueous solution or an organic solvent solution was added, and the temperature thereof was made to 25 to 90° C., and then the solvent was remove by evaporation under reduced pressure, and dried to obtain the titled compound as an amorphous.

Example 7(2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide hydrochloride (D-Type Crystal)

The compound (40 mg) produced in Example 7(1) was placed in 10-mL test tube, and methanol (1.2 mL) was added thereto, followed by being stirred at 40 to 60° C. The reaction solution was cooled to room temperature, and the obtained crystals were collected by filtration, and dried overnight at 60° C. to obtain the titled compound (10 mg) as a white crystal.

Example 7(3)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide hydrochloride (B-Type Crystal)

The compound (5 mg) produced in Example 7(1) was placed in 10-mL test tube, and acetone (0.6 mL) was added thereto, followed by being stirred at 40 to 60° C. The reaction solution was cooled to room temperature, and the obtained crystals were collected by filtration, and dried overnight at 60° C. to obtain the titled compound (3 mg) as a white crystal.

Example 8

N-{5-[(6,7-dimethoxy-4-quinolinyl)oxy]-2-pyridinyl}-2,5-dioxo-1-phenyl-1,2,5,6,7,8-hexahydro-3-quinolinecarboxamide methanesulfonate (A-Type Crystal)

In a 10-mL flask, the compound A (100 mg) produced in Example 5 was placed, and acetone (3 mL) was added thereto, followed by being stirred at 40 to 55° C. Methane sulfonic acid (12 μL) was added to this reaction solution, and the obtained crystals were collected by filtration and dried overnight at 75° C. Thus, the titled compound (112 mg) having the following physical property value was obtained as a white crystal.

LC-MS: 563 (M+H)$^+$;
$^1$H-NMR (DMSO-d$_6$): δ 1.94-2.06, 2.31, 2.47-2.55, 4.03, 4.05, 7.04, 7.44-7.51, 7.55, 7.58-7.70, 7.76, 8.01, 8.46-8.54, 8.84, 8.99, 12.05.

Example 8(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide methanesulfonate (B-Type Crystal)

The compound produced in Example 8 was added to a mixed solvent (for example, a mixed solvent of methanol and dioxane), dissolved at 40 to 80° C., then cooled to generated crystals. The generated crystals were isolated and dried to obtain the titled compound as crystals.

Example 8(2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide methanesulfonate (C-Type Crystal)

The compound A produced in Example 5 was dissolved in a solvent (for example, methanol), and methanesulfonic acid was added to the solution. Then, the solvent was concentrated, and a solvent (for example, methanol) was added to a residue. The resultant product was heated to 30 to 50° C. and allowed to stand still for four hours. The generated crystals were isolated and dried to obtain the titled compound as crystals.

Example 9

N-{5-[(6,7-dimethoxy-4-quinolinyl)oxy]-2-pyridinyl}-2,5-dioxo-1-phenyl-1,2,5,6,7,8-hexahydro-3-quinolinecarboxamide p-toluenesulfonate (C-Type Crystal)

In a 300-mL flask, the compound (5 g) produced in Example 5 was placed, and acetone (135 mL) was added thereto, followed by being stirred at 40 to 55° C. To this reaction solution, a solution of p-toluenesulfonic acid-monohydrate (1.86 g) in acetone (15 mL) was added. The resultant solution was stirred. The obtained crystals were collected by filtration, and dried to obtain crude crystals. To the crude crystals (1 g), 10% hydrated acetone (12 mL) was added, and stirred at 40 to 55° C. The obtained crystals were collected by filtration, and dried overnight at 75° C. to obtain the titled compound (0.7 g) having the following physical property value as a white crystal.

LC-MS: 563 (M+H)$^+$;
$^1$H-NMR (DMSO-d$_6$): δ 1.93-2.06, 2.28, 2.40-2.59, 4.03, 4.04, 7.02, 7.10, 7.43-7.50, 7.52, 7.56-7.69, 7.76, 8.00, 8.45-8.53, 8.83, 8.99, 12.05.

Example 9(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide p-toluenesulfonate (A-Type Crystal)

The compound produced in Example 9 was added to a mixed solvent (for example, a mixed solvent of tetrahydrofuran and water) and dissolved at 50 to 70° C. Then, the resultant product was cooled. Then, the generated crystals were isolated and dried to obtain the titled compound as crystals.

Example 9 (2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide p-toluenesulfonate (B-Type Crystal)

To the compound A produced in Example 5, a solvent (for example, acetone) and p-toluenesulfonic acid monohydrate were added and heated to 30 to 50° C. and stirred. Then, the generated crystals are isolated and dried to obtain the titled compound as crystals.

Example 9(3)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide p-toluenesulfonate (G-Type Crystal)

The compound produced in Example 9 was added to a mixed solvent (for example, a mixed solvent of ethanol and water), the resultant solution was heated to 60 to 80° C. and stirred for 12 hours or more. Then, the generated crystals were isolated and dried to obtain the titled compound as crystals.

Example 9 (4)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide p-toluenesulfonate (H-Type Crystal)

To the compound A produced in Example 5, a mixed solvent (for example, mixed solvent of water and acetone), and p-toluenesulfonic acid monohydrate were added and dissolved at 30 to 50° C., stirred, and the cooled. Then, the generated crystals are isolated and dried to obtain the titled compound as crystals.

Example 10

N-{5-[(6,7-dimethoxy-4-quinolinyl)oxy]-2-pyridinyl}-2,5-dioxo-1-phenyl-1,2,5,6,7,8-hexahydro-3-quinolinecarboxamide sulfate (A-Type Crystal)

The compound A (0.9 g) produced in Example 5 was placed in 100-mL flask, acetone (27 mL) was added thereto, followed by being stirred at 40 to 55° C. To this reaction solution, 0.25 mol/L sulfuric acid aqueous solution (370 µL) was added, and the obtained crystals were collected by filtration, and dried overnight at 75° C. to obtain the titled compound (107 mg) having the following physical property value as a white crystal.

LC-MS: 563 $(M+H)^+$;
$^1$H-NMR (DMSO-$d_6$): δ 1.94-2.06, 2.41-2.61, 4.00-4.08, 6.98-7.05, 7.43-7.55, 7.57-7.70, 7.73-7.78, 7.96-8.04, 8.44-8.54, 8.78-8.86, 8.97-9.01, 12.02-12.07.

Example 10(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide sulfate (B-Type Crystal)

The compound produced in Example 10 was added to a mixed solvent (for example, a mixed solvent of dimethylsulfoxide and water) and dissolved therein at 70 to 90° C., then cooled to generate crystals. The generated crystals were isolated and dried to obtain the titled compound as crystals.

Example 10(2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide sulfate (C-Type Crystal)

To the compound A produced in Example 5, a solvent (for example, acetone) and sulfuric acid were added and heated to 30 to 50° C. and stirred. Then, the generated crystals are isolated and dried to obtain the titled compound as crystals.

Example 11

N-{5-[(6,7-dimethoxy-4-quinolinyl)oxy]-2-pyridinyl}-2,5-dioxo-1-phenyl-1,2,5,6,7,8-hexahydro-3-quinolinecarboxamide phosphate (A-Type Crystal)

The compound A (0.10 g) produced in Example 5 was placed in 10-mL flask, acetone (3 mL) and 85% phosphoric acid (22 mg) were added thereto, followed by being stirred at 40 to 55° C. The obtained crystals were collected by filtration, and dried at 90° C. for one hour to obtain the titled compound (0.11 g) having the following physical property value as a white crystal.

LC-MS: 563 $(M+H)^+$;
$^1$H-NMR (DMSO-$d_6$): δ 1.95-2.04, 2.47-2.56, 3.93, 3.95, 6.55, 7.41, 7.45-7.49, 7.52, 7.56-7.68, 7.87, 8.34-8.37, 8.40-8.45, 8.49, 8.98, 11.97.

Example 11(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide phosphate (B-Type Crystal)

To the compound A produced in Example 5, a solvent (for example, methanol) and phosphoric acid were added, and the resultant product was heated to 30 to 50° C., and stirred to generate crystals. The generated crystals were isolated and dried to obtain the titled compound as crystals.

Example 11(2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide phosphate (C-Type Crystal)

To the compound A produced in Example 5, a solvent (for example, tetrahydrofuran) and phosphoric acid were added, and the resultant product was heated to 40 to 60° C., and stirred to generate crystals. The generated crystals were isolated and dried to obtain the titled compound as crystals.

Example 11(3)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide phosphate (D-Type Crystal)

To the compound A produced in Example 5, a solvent (for example, 2-propanol) and phosphoric acid were added, and the resultant product was heated to 60 to 80° C., and stirred to generate crystals. The generated crystals were isolated and dried to obtain the titled compound as crystals.

Example 11(4)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide phosphate (E-Type Crystal)

To the compound A produced in Example 5, a solvent (for example, ethanol) and phosphoric acid were added, and the resultant product was heated to 50 to 70° C., and stirred to generate crystals. The generated crystals were isolated and dried to obtain the titled compound as crystals.

Example 12

N-{5-[(6,7-dimethoxy-4-quinolinyl)oxy]-2-pyridinyl}-2,5-dioxo-1-phenyl-1,2,5,6,7,8-hexahydro-3-quinolinecarboxamide benzenesulfonate (A-Type Crystal)

The compound A (0.10 g) produced in Example 5 was placed in 10-mL flask, acetone (3 mL) and benzenesulfonic acid (30 mg) were added thereto, followed by being stirred at 40 to 55° C. The obtained crystals were collected by filtration, and dried at 90° C. for one hour to obtain the titled compound (0.11 g) having the following physical property value as a white crystal.

LC-MS: 563 (M+H)$^+$;
$^1$H-NMR (DMSO-d$_6$): δ 1.95-2.05, 2.47-2.56, 4.03, 4.05, 7.04, 7.28-7.34, 7.45-7.49, 7.53, 7.57-7.62, 7.62-7.68, 7.77, 8.01, 8.47-8.52, 8.84, 9.00, 12.06.

Example 12(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide benzenesulfonate (B-Type Crystal)

The compound A produced in Example 5 was dissolved in a solvent (for example, methanol), and benzenesulfonic acid was added thereto. Then, the solvent was concentrated, and a solvent (for example, ethanol) was added to a residue. The resultant product was heated to 30 to 50° C. and allowed to stand still for four hours. The generated crystals were isolated and dried to obtain the titled compound as crystals.

Example 12(2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide benzenesulfonate (C-Type Crystal)

The compound A produced in Example 5 was dissolved in a solvent (for example, methanol), and benzenesulfonic acid was added. Then, the solvent was concentrated, and a solvent (for example, tetrahydrofuran) was added to a residue. The resultant product was heated to 30 to 50° C. and allowed to stand still for four hours. The generated crystals were isolated and dried to obtain the titled compound as crystals.

Example 12(3)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide benzenesulfonate (D-Type Crystal)

The compound A produced in Example 5 was dissolved in a solvent (for example, methanol), and benzenesulfonic acid was added. Then, the solvent was concentrated, and a solvent (for example, acetonitrile) was added to a residue. The resultant product was heated to 30 to 50° C. and allowed to stand still for four hours. The generated crystals were isolated and dried to obtain the titled compound as crystals.

Example 13

N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanedisulfonate (A-Type Crystal)

The compound A (0.8 g) produced in Example 5 was placed in 30-mL flask, acetone (24 mL) and a solution of ethanedisulfonic acid (386 mg) in acetone (24 mL) were added thereto, followed by being stirred at 40 to 55° C. The obtained crystals were collected by filtration, and dried at 90° C. overnight to obtain the titled compound (1.1 g) having the following physical property value as a light yellowish brown crystal.

LC-MS: 563 (M+H)$^+$;
$^1$H-NMR (DMSO-d$_6$): δ 1.94-2.06, 2.45-2.55, 2.68, 4.04, 4.06, 7.08, 7.44-7.50, 7.56-7.70, 7.78, 8.02, 8.47-8.53, 8.87, 8.99, 12.06.

Example 13(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanedisulfonate (B-Type Crystal)

The compound A produced in Example 5 was dissolved in a solvent (for example, methanol) and ethanedisulfonic acid was added. Then, the solvent was concentrated, and a solvent (for example, acetonitrile) was added to a residue. The resultant product was heated to 30 to 50° C. and allowed to stand still for four hours. The generated crystals were isolated and dried to obtain the titled compound as crystals.

Example 13(2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanedisulfonate (C-Type Crystal)

The compound A produced in Example 13 was added to a solvent (for example, ethyl acetate), heated at 60 to 80° C., and stirred for 20 minutes or more. Then the generated crystals were isolated and dried to obtain the titled compound as crystals.

Example 13(3)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanedisulfonate (D-Type Crystal)

The compound produced in Example 13 was added to a solvent (for example, dimethyl acetamide), heated at 60 to 80° C., and stirred for 20 minutes or more. Then, the generated crystals were isolated and dried to obtain the titled compound as crystals.

Example 13(4)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanedisulfonate (E-Type Crystal)

The compound produced in Example 13 was added to a solvent (for example, tetrahydrofuran), heated at 40 to 60° C., and stirred for 20 minutes or more. Then, the generated crystals were isolated and dried to obtain the titled compound as crystals.

Example 14

N-{5-[(6,7-dimethoxy-4-quinolinyl)oxy]-2-pyridinyl}-2,5-dioxo-1-phenyl-1,2,5,6,7,8-hexahydro-3-quinolinecarboxamide isethionate (A-Type Crystal)

The compound A (0.3 g) produced in Example 5 was placed in 100-mL flask, acetone (48 mL), isethionic acid (96 mg), and water (3 mL) were added thereto, followed by being stirred at room temperature. This reaction solution was filtrated, filtrate was concentrated, and small amount of acetonitrile was added and further concentrated, and dried overnight at room temperature to obtain the titled compound (375 mg) having the following physical property value as a pale yellow crystal.
LC-MS: 563 (M+H)$^+$;
$^1$H-NMR (DMSO-d$_6$): δ 1.95-2.06, 2.47-2.53, 2.60, 3.62, 4.03, 4.05, 7.02, 7.44-7.50, 7.53, 7.56-7.69, 7.76, 8.00, 8.46-8.53, 8.83, 9.00, 12.05.

Example 14(1)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide isethionate (B-Type Crystal)

The compound A produced in Example 5 was dissolved in a solvent (for example, methanol) and isethionic acid was added. Then, the solvent was concentrated, and a solvent (for example, ethanol) was added to a residue. The resultant product was heated to 30 to 50° C. and allowed to stand still for four hours. The generated crystals were isolated and dried to obtain the titled compound as crystals.

Example 14(2)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide isethionate (C-Type Crystal)

The compound A produced in Example 5 was dissolved in a solvent (for example, methanol) and isethionic acid was added. Then, the solvent was concentrated, and a solvent (for example, acetonitrile) was added to a residue. The resultant product was heated to 30 to 50° C. and allowed to stand still for four hours. The generated crystals were isolated and dried to obtain the titled compound as crystals.

Example 14(3)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide isethionate (D-Type Crystal)

The compound A produced in Example 5 was dissolved in a solvent (for example, methanol) and isethionic acid was added. Then, the solvent was concentrated, and a solvent (for example, methanol) was added to a residue. The resultant product was heated to 30 to 50° C. and allowed to stand still for four hours. The generated crystals were isolated and dried to obtain the titled compound as crystals.

Example 14(4)

N-{5-[(6,7-dimethoxy-4-quinolinyl)oxy]-2-pyridinyl}-2,5-dioxo-1-phenyl-1,2,5,6,7,8-hexahydro-3-quinolinecarboxamide isethionate (E-Type Crystal)

The compound A produced in Example 5 was dissolved in a solvent (for example, methanol) and isethionic acid was added. Then, the solvent was concentrated, and a solvent (for example, tetrahydrofuran) was added to a residue. The resultant product was heated to 30 to 50° C. and allowed to stand still for four hours. The generated crystals were isolated and dried to obtain the titled compound as crystals.

Experiment Example

The following is physicochemical experiment examples. Based on these experiment methods, the effects of compounds of the present invention were verified.

Physicochemical Experiment Example 1: Evaluation of Hygroscopicity (DVS)

Various acid addition salts of the compounds A produced in Examples (Examples 7, 8, 9, 10, 11, 12, 13, and 14) and the compound of the present invention (Example 6) were subjected to hygroscopicity evaluation. Based on the measurement conditions shown in [3] in [Study of acid addition salt of compound A], hygroscopicity was evaluated. Sample weight was recorded after the weight of the sample in the relative humidity set every 10% became equilibrium. After drying, the change amount (%) was converted on the basis of the weight when the relative humidity was 0%. Results are shown in Table 3.

TABLE 3

| Acid addition salt | Weight increase at relative humidity of 90% (%) |
|---|---|
| Ethanesulfonate | 0.7 |
| Hydrochloride | 8.0 |
| Methanesulfonate | 4.0 |
| P-toluenesulfonate | 2.6 |
| Sulfate | 7.2 |
| Phosphate | 5.5 |
| Benzensuplhonate | 7.2 |
| Ethanedisulfonate | 46.4 |
| Isethionate | 14.5 |

As a result, in various acid addition salts of the compound A, only the compound of the present invention, that is, ethanesulfonate of the compound A was found to have a small rate of weight change upon moisture absorption and to be highly stable and useful as an active pharmaceutical ingredient.

Physicochemical Experiment Example 2:
Evaluation of Light Stability (1) Light Stability Evaluation of Active Pharmaceutical Ingredient Ethanesulfonate of the compound A produced in Example 6 and p-toluenesulfonate of the compound A produced in Example 9 were evaluated in terms of the light stability. Each acid addition salt was weighed in a laboratory tube in about 1.8 to 2.2 mg, capped with a plastic cap and wrapped with a parafilm. A sample placed in the transparent laboratory tube was used as an exposure sample, a sample placed in the brown laboratory tube was used as a light shielded sample, and a sample placed in the brown laboratory tube and further covered with aluminum foil was used as an aluminum foil completely shielded sample. Each sample was exposed to light whose total illumination of 1200000 Lux·h or more and total near ultraviolet radiation energy of 200 W·h/m$^2$ or more by exposing to 2500 Lux D65 lamp at 25° C. for 20 days.

(Measurement Conditions)
Detector: ultraviolet spectrometer (measurement wavelength: 215 nm),
Column: Imtakt Unison UK-C18 (3 μm, inner diameter: 4.6 mm×150 mm),
Column temperature: 40° C.,
Mobile phase: A liquid: 20 mM KH$_2$PO$_4$ aq. (pH 3.0), B liquid: CH$_3$CN,
A/B=80/20 (0 minutes)→20/80 (60 minutes),
Flow rate: 1.0 mL/minute,
Area measurement range: 60 minutes
Infusion amount: 5 μL,
Sample concentration: 0.5 mg/mL.

The area percentage of ethanesulfonate of the compound A and p-toluenesulfonate of the compound A which were not exposed to light and stored at −20° C., and each acid addition salt of the compound A subjected to the above light stability test were calculated under the measurement conditions mentioned above. Next, in each acid addition salt of the compound A, the rate of the area percentage of the acid addition salt of the compound A which was not exposed to light and stored at −20° C. (area percentage of acid addition salt of compound A exposed to light for 20 days/area percentage of acid addition salt of compound A which is not exposed to light and stored at −20° C.×100) was calculated as the residual rate of each compound. The results are shown in Table 4.

TABLE 4

|  | Ethanesulfonate of compound A (residual rate %) | p-toluenesulfonate of compound A (residual rate %) |
| --- | --- | --- |
| Transparent bottle | 94.5 | 86.1 |
| Brown bottle | 99.5 | 92.7 |
| Aluminum foil shielding | 100.0 | 100.6 |

(2) Evaluation of Stability of Simple Formulation

Each acid addition salt of the compound A, regarding to ethanesulfonate of the compound A produced in Example 6 and p-toluenesulfonate of the compound A produced in Example 9, was mixed with CEOLUS (registered trademark) PH-301 (Asahi Kasei Corporation) in a mixing ratio of 1 to 5 (weight ratio) on a medicine paper with a spatula to prepare a simple formulation. The simple formulation was weighed into a laboratory tube in about 3 mg, capped with a plastic cap, and wrapped with a parafilm. Hereinafter, the light exposure condition of the compound, and the measurement conditions were corresponding to the evaporation of the stability of the active pharmaceutical ingredient of above (1). The results are shown in Table 5.

TABLE 5

|  | Ethanesulfonate of compound A (residual rate %) | p-toluenesulfonate of compound A (residual rate %) |
| --- | --- | --- |
| Transparent bottle | 59.3 | 40.7 |
| Brown bottle | 98.4 | 83.3 |
| Aluminum foil shielding | 99.7 | 99.9 |

The results mentioned above showed that the ethanesulfonate of the compound A was more excellent also in terms of the stability to light as compared with that of the p-toluenesulfonate of the compound A.

Formulation Examples

Formulation Example 1

The components indicated below were mixed by a standard method, followed by making the mixture into tablets to obtain 10,000 tablets each containing 10 mg of active ingredient.
N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate . . . 100 g
calcium carboxymethyl cellulose (disintegrant) . . . 20 g
magnesium stearate (lubricant) . . . 10 g
microcrystalline cellulose . . . 870 g Formulation Example 2

The components indicated below were mixed by a standard method, filtered through a dust-removing filter, filled into ampoules so that each ampoule contains 5 ml, and thermally sterilized in an autoclave to obtain 10,000 ampoules each containing 20 mg active ingredient.
N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate . . . 200 g
mannitol . . . 20 g
distilled water . . . 50 L

INDUSTRIAL APPLICABILITY

The compound of the present invention has an Axl-selective inhibiting activity and low CYP inhibitory action, and shows a low hygroscopicity in various acid addition salts of the compound A, and is a stable salt with respect to humidity. Therefore, the compound of the present invention is useful as an active pharmaceutical ingredient of an agent for preventing and/or treating diseases related to expression of Axl.

The invention claimed is:
1. N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate.
2. A crystal of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate.
3. The crystal according to claim 2, wherein in a powder X-ray diffraction spectrum, the crystal has peaks at 2θ of about 7.3, about 7.9, about 9.1, about 10.7, about 11.2, about

12.5, about 13.4, about 15.6, about 16.2, about 16.5, about 17.7, about 18.0, about 18.4, about 19.1, about 20.1, about 20.8, about 21.2, about 21.5, about 22.4, about 23.0, about 23.6, and about 24.0.

4. The crystal according to claim 2, which produces a powder X-ray diffraction spectrum chart as shown in FIG. 1.

5. The crystal according to claim 2, wherein in differential scanning calorimetry, the crystal has an endothermic peak of an onset temperature of about 283° C. or a peak temperature of about 286° C.

6. The crystal according to claim 2, which produces a differential scanning calorimetry chart as shown in FIG. 2.

7. A pharmaceutical composition comprising N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate or a crystal thereof, and a pharmaceutically acceptable carrier.

8. A method for treating an Axl-related disease in a subject in need thereof, comprising administering to the subject an effective amount of N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate or a crystal thereof.

9. The method according to claim 8, which comprises administering said N-{5-[(6,7-dimethoxy-4-quinolinyl)oxy]-2-pyridinyl}-2,5-dioxo-1-phenyl-1,2,5,6,7,8-hexahydro-3-quinolinecarboxamide ethanesulfonate or crystal thereof in a pharmaceutical composition together with a pharmaceutically acceptable carrier.

10. The method according to claim 9, wherein the pharmaceutical composition is an Axl inhibitor.

11. The method according to claim 10, wherein the Axl-related disease is cancer, an immune system disease, or a circulatory system disease.

12. The method according to claim 11, wherein the cancer is leukemia, malignant lymphoma, multiple myeloma, myelodysplastic syndromes, melanoma, uveal malignant melanoma, head and neck cancer, esophageal cancer, esophageal adenocarcinoma, stomach cancer, large intestine cancer, colon cancer, rectal cancer, liver cancer, gallbladder and bile duct cancer, biliary tract cancer, pancreatic cancer, thyroid cancer, lung cancer, breast cancer, ovarian cancer, cervical cancer, uterine body cancer, endometrial cancer, vaginal cancer, vulvar cancer, renal cell carcinoma, urothelial carcinoma, prostate cancer, testicular tumor, bone and soft tissue sarcoma, skin cancer, glioma, brain tumors, pleural mesothelioma or cancer of unknown primary.

* * * * *

UNITED STATES PATENT AND TRADEMARK OFFICE
CERTIFICATE OF CORRECTION

PATENT NO. : 10,836,747 B2
APPLICATION NO. : 16/480514
DATED : November 17, 2020
INVENTOR(S) : Takahiro Nekado et al.

It is certified that error appears in the above-identified patent and that said Letters Patent is hereby corrected as shown below:

In the Claims

In Claim 3, Column 30, Line 66, delete "20" and insert --2θ-- therefor.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*